US011351306B2

(12) United States Patent
Swantner et al.

(10) Patent No.: US 11,351,306 B2
(45) Date of Patent: Jun. 7, 2022

(54) SYRINGE PLUNGER WITH DYNAMIC SEAL

(71) Applicant: BAYER HEALTHCARE LLC, Whippany, NJ (US)

(72) Inventors: Michael Swantner, Saxonburg, PA (US); Michael McDermott, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 237 days.

(21) Appl. No.: 16/471,300

(22) PCT Filed: Jan. 4, 2018

(86) PCT No.: PCT/US2018/012284
§ 371 (c)(1),
(2) Date: Jun. 19, 2019

(87) PCT Pub. No.: WO2018/129116
PCT Pub. Date: Jul. 12, 2018

(65) Prior Publication Data
US 2020/0086057 A1     Mar. 19, 2020

Related U.S. Application Data

(60) Provisional application No. 62/443,302, filed on Jan. 6, 2017.

(51) Int. Cl.
*A61M 5/315* (2006.01)
*A61M 5/31* (2006.01)

(52) U.S. Cl.
CPC . *A61M 5/31513* (2013.01); *A61M 2005/3123* (2013.01); *A61M 2207/00* (2013.01)

(58) Field of Classification Search
CPC ...... A61M 5/31513; A61M 2005/3123; A61M 5/315; A61M 5/31511; A61M 5/31515;
(Continued)

(56) References Cited

U.S. PATENT DOCUMENTS

| 4,180,069 A | * | 12/1979 | Walters | ............ A61M 5/31515 |
| | | | | 604/228 |
| 5,558,855 A | | 9/1996 | Quay | |

(Continued)

FOREIGN PATENT DOCUMENTS

| EP | 1166807 A1 | 1/2002 |
| WO | 2006109272 A2 | 10/2006 |

(Continued)

OTHER PUBLICATIONS

"International Preliminary Report on Patentability from PCT Application No. PCT/US2018/012284", dated Jul. 18, 2019.

*Primary Examiner* — Bhisma Mehta
*Assistant Examiner* — Nidah Hussain
(74) *Attorney, Agent, or Firm* — Joseph L. Kent; David Schramm; James R. Stevenson

(57) ABSTRACT

A plunger, a syringe, and a method of making a plunger and a syringe are disclosed. The plunger includes a support ring and a cover disposed over and coupled to the support ring. A cavity defining a predetermined volume is defined between the support ring and the cover. The syringe includes a barrel defining an inner wall and the plunger inserted therein.

20 Claims, 17 Drawing Sheets

(58) Field of Classification Search
CPC .............. A61M 5/007; A61M 5/14546; A61M 5/14566; A61M 2005/31521; A61M 2005/3131; A61M 2205/0222
USPC ........................................................ 604/222
See application file for complete search history.

(56) References Cited

U.S. PATENT DOCUMENTS

| | | | |
|---|---|---|---|
| 6,432,089 B1* | 8/2002 | Kakimi | ............ A61M 5/14546 604/218 |
| 6,984,222 B1 | 1/2006 | Hitchins et al. | |
| 7,666,169 B2 | 2/2010 | Cowan et al. | |
| 7,682,345 B2 | 3/2010 | Savage | |
| 8,945,051 B2 | 2/2015 | Stokes, Jr. et al. | |
| 9,173,995 B1 | 11/2015 | Tucker et al. | |
| 9,199,033 B1 | 12/2015 | Cowan et al. | |
| 9,480,797 B1 | 11/2016 | Swantner | |
| 9,700,670 B2 | 7/2017 | Tucker et al. | |
| 2004/0064041 A1 | 4/2004 | Lazzaro et al. | |
| 2005/0182371 A1* | 8/2005 | Wagner | .............. A61M 5/31511 604/218 |
| 2007/0219508 A1 | 9/2007 | Bisegna et al. | |
| 2010/0130935 A1 | 5/2010 | Hieb et al. | |
| 2016/0151570 A1 | 6/2016 | Rhinehart et al. | |
| 2016/0325048 A1 | 11/2016 | Berry et al. | |
| 2017/0209648 A1 | 7/2017 | Butts et al. | |

FOREIGN PATENT DOCUMENTS

| | | |
|---|---|---|
| WO | 2010139793 A1 | 12/2010 |
| WO | 2018129116 A1 | 7/2018 |

* cited by examiner

SYRINGE PLUNGER WITH DYNAMIC SEAL

CROSS REFERENCE TO RELATED APPLICATIONS

This application is a § 371 U.S. national phase application of PCT International Application No. PCT/US2018/012284, filed 4 Jan. 2018, and claims the benefit of U.S. Provisional Patent Application No. 62/443,302, filed 6 Jan. 2017, the disclosures of which are incorporated herein by reference in their entirety.

TECHNICAL FIELD

The present disclosure relates generally to medical fluid delivery applications, and, particularly, to fluid injection systems including a fluid injector, a syringe, and a plunger within the syringe. More particularly, the present disclosure is directed to a syringe plunger with a dynamic seal.

BACKGROUND

In many medical diagnostic and therapeutic procedures, a medical practitioner such as a physician injects a patient with a fluid. In recent years, a number of injector-actuated syringes and powered injectors for pressurized injection of fluids, such as contrast media, have been developed for use in imaging procedures such as angiography, computed tomography (CT), ultrasound, and magnetic resonance imaging. In general, these powered injectors are designed to deliver a preset amount of contrast and/or saline at a preset flow rate using one or more disposable or refillable syringes.

Automatic injection mechanisms typically include a syringe connected to a powered injector with a linear actuator. The linear actuator operates a moveable piston that is configured to engage a plunger inserted in the barrel of the syringe. The interface or engagement between the piston and plunger generally includes a reversible mechanical locking structure such as screw threads, undercuts, pins, swivels, snap fit connections, and the like for establishing and maintaining the connection between the piston and plunger.

The plunger/piston interface should be sufficiently strong to retract the plunger in a proximal direction through the barrel to draw fluid into the syringe, as well as to advance the plunger through the barrel in the distal direction to expel the fluid contained therein.

In addition to being sufficiently strong to maintain good connection between the piston and plunger during use, the interface should also be removable so that the syringe and plunger can be disposed of after use. With mechanical locking structures, to disengage the piston from the plunger, the user either orients the piston and plunger for disengagement, such as by rotating the syringe to properly align locking features on the piston and plunger, or pulls the piston away from the plunger with sufficient force to overcome the locking structure. Once the piston is disengaged from the plunger, the used syringe and plunger may be discarded.

A challenge with syringe plunger seals is insufficient sealing during injection procedures. It would be desirable to provide a syringe plunger with a dynamic seal enhance sealing during injection procedures where compression is generated when the syringe is under injection pressure conditions. Preloading compression is not desirable because over the shelf life of the syringe the plastic components undergo deformation or creep that impairs forming an adequate seal under injection pressure conditions. Furthermore, it is desirable to limit compression due to automated assembly process where it is desirable to have low pressure during manufacturing. Accordingly, various aspects of a syringe plunger with a dynamic seal described herein overcome these deficiencies.

SUMMARY

While automated injectors are well-known, improved fluid delivery systems which make the injection processes simpler for medical staff are always needed. With respect to the present disclosure, a syringe having a plunger with a dynamic seal is set forth. Desirably, the plunger with a dynamic seal which slides easily through the inner wall of the barrel of the syringe, but nevertheless is configured to provide a good effective seal against the inner wall of the barrel during an injection procedure to prevent leaking of the substance contained therein, is also needed.

In view of the foregoing, a need exists for a syringe having a plunger with a dynamic seal which can be used with an injector, such as a powered injector. According to one aspect of the disclosure, the plunger with dynamic seal generates compression under injection pressure conditions. Initially, under relatively low pressure conditions, the compression between the plunger and the inner wall of the barrel is low. The compression increases under injection pressure conditions of the fluid delivery system and thus increases the seal between the plunger and the inner wall of the barrel of the syringe.

In one aspect, a syringe plunger with a dynamic seal is provided. The syringe plunger with a dynamic seal comprises a support ring and a cover disposed over and coupled to the support ring, wherein an air cavity defining a predetermined volume is defined between the support ring and the cover.

In another aspect, a syringe comprising a plunger with a dynamic seal is provided. The syringe comprises a barrel defining an inner wall, and a plunger located within the inner of the barrel. The plunger comprises a support ring and a cover disposed over and coupled to the support ring, wherein an air cavity defining a predetermined volume is defined between the support ring and the cover.

In addition to the foregoing, various other method and/or system and/or program product aspects are set forth and described in the teachings, such as text (e.g., claims and/or detailed description) and/or drawings of the present disclosure.

The various aspects of the present disclosure are also described in the following clauses.

Clause 1: A plunger, comprising: a support ring; and a cover disposed over and coupled to the support ring, wherein the support ring and the cover define an air cavity therebetween, the air cavity defining a predetermined volume.

Clause 2: The plunger of clause 1, further comprising a conical cap disposed over the cover.

Clause 3: The plunger of clause 2, wherein the conical cap comprises an overmold element disposed over thereon.

Clause 4: The plunger of any of clauses 1 to 3, wherein the cover further comprises first and second annular ribs.

Clause 5: The plunger of any of clauses 1 to 4, wherein the cover comprises: conical cap; a cylindrical sidewall having at least one annular rib; and a flange to engage the support ring.

Clause 6: The plunger of any of clauses 1 to 5, wherein the support ring comprises a conical cap that defines an included angle greater than about 90°.

Clause 7: The plunger of clause 6, wherein the conical cap of the support ring defines an included angle greater than about 90° and less than about 120°.

Clause 8: The plunger of clause 6 or 7, wherein the conical cap of the support ring and the conical cap of the cover define an angle therebetween.

Clause 9: The plunger of clause 8, wherein the angle defined between the conical cap of the support ring and the conical cap of the cover is greater than 0° and less than about 30°.

Clause 10: The plunger of any of clauses 1 to 9, wherein the support ring comprises: a shoulder; and defines an annular groove between the shoulder and the conical cap to receive a flange defined by the cover.

Clause 11: The plunger of any of clauses 1 to 10, wherein the predetermined volume is selected in a range between 0.1 mL and 10 mL.

Clause 12: A syringe, comprising: a barrel defining an inner wall; and a plunger located within the inner wall of the barrel, the plunger comprising: a support ring; and a cover disposed over and coupled to the support ring, wherein an air cavity defining a predetermined volume is defined between the support ring and the cover.

Clause 13: The syringe of clause 12, wherein the plunger comprises a conical cap disposed over the cover.

Clause 14: The syringe of clause 13, wherein the conical cap comprises an overmold element disposed thereon.

Clause 15: The syringe of any of clauses 12 to 14, wherein the cover further comprises first and second annular ribs that form a seal with the inner wall of the barrel.

Clause 16: The syringe of any of clauses 12 to 15, wherein the cover comprises: conical cap; a cylindrical sidewall having at least one annular rib; and a flange to engage the support ring.

Clause 17: The syringe of any of clauses 12 to 16, wherein the support ring comprises a conical cap that defines an included angle greater than about 90°.

Clause 18: The syringe of clause 17, wherein the conical cap of the support ring defines an included angle greater than about 90° an d less than about 120°.

Clause 19: The syringe of clause 17 or 18, wherein the conical cap of the support ring and the conical cap of the cover define an angle therebetween.

Clause 20: The syringe of clause 19, wherein the angle defined between the conical cap of the support ring and the conical cap of the cover is greater than 0° and less than about 30°.

Clause 21: The syringe of any of clauses 12 to 20, wherein the support ring comprises: a shoulder; and defines an annular groove between the shoulder and the conical cap to receive a flange defined by the cover.

Clause 22: The syringe of any of clauses 12 to 21, wherein the predetermined volume is selected in a range between 0.1 mL and 10 mL.

Clause 23: A method of making a plunger, the method comprising: providing a support ring, the support ring comprising a first conical cap, a shoulder, and defines an annular groove between the shoulder and the conical cap; attaching a cover to the support ring, the cover comprising a second conical cap, a cylindrical sidewall, and a flange to engage the annular groove of the support ring; and attaching a third conical cap to the second conical cap of the cover.

Clause 24: A method of making a syringe, comprising: providing a syringe barrel; making a plunger in accordance with a method, the method comprising: providing a support ring, the support ring comprising a first conical cap, a shoulder, and defines an annular groove between the shoulder and the conical cap; attaching a cover to the support ring, the cover comprising a second conical cap, a cylindrical sidewall, and a flange to engage the annular groove of the support ring; and attaching a third conical cap to the second conical cap of the cover; and inserting the plunger in the syringe barrel.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

Further, it is understood that any one or more of the following-described forms, expressions of forms, examples, can be combined with any one or more of the other following-described forms, expressions of forms, and examples.

The foregoing summary is illustrative only and is not intended to be in any way limiting. In addition to the illustrative aspects, aspects, and features described above, further aspects, aspects, and features will become apparent by reference to the drawings and the following detailed description.

FIGURES

The novel features of the described forms are set forth with particularity in the appended claims. The described forms, however, both as to organization and methods of operation, may be best understood by reference to the following description, taken in conjunction with the accompanying drawings in which:

FIG. 6 is a perspective view of the support ring, according to one aspect of the present disclosure;

FIG. 7 is a perspective view of the support ring, according to one aspect of the present disclosure;

FIG. 8 is a plan view of the supporting ring, according to one aspect of the present disclosure;

FIG. 9 is an elevational view of the support ring, according to one aspect of the present disclosure;

FIG. 10 is a bottom view of the support ring, according to one aspect of the present disclosure;

FIG. 11 is a sectional view of the support ring taken along section line 11-11, as shown in FIG. 10, according to one aspect of the present disclosure;

DESCRIPTION

Before explaining various forms of syringe plungers with dynamic seals in detail, it should be noted that the illustrative forms are not limited in application or use to the details of construction and arrangement of parts illustrated in the accompanying drawings and description. The illustrative forms may be implemented or incorporated in other forms, variations and modifications, and may be practiced or carried out in various ways. Further, unless otherwise indicated, the terms and expressions employed herein have been chosen for the purpose of describing the illustrative forms for the convenience of the reader and are not for the purpose of limitation thereof.

Further, it is understood that any one or more of the following-described forms, expressions of forms, examples, can be combined with any one or more of the other following-described forms, expressions of forms, and examples.

Figure 1:
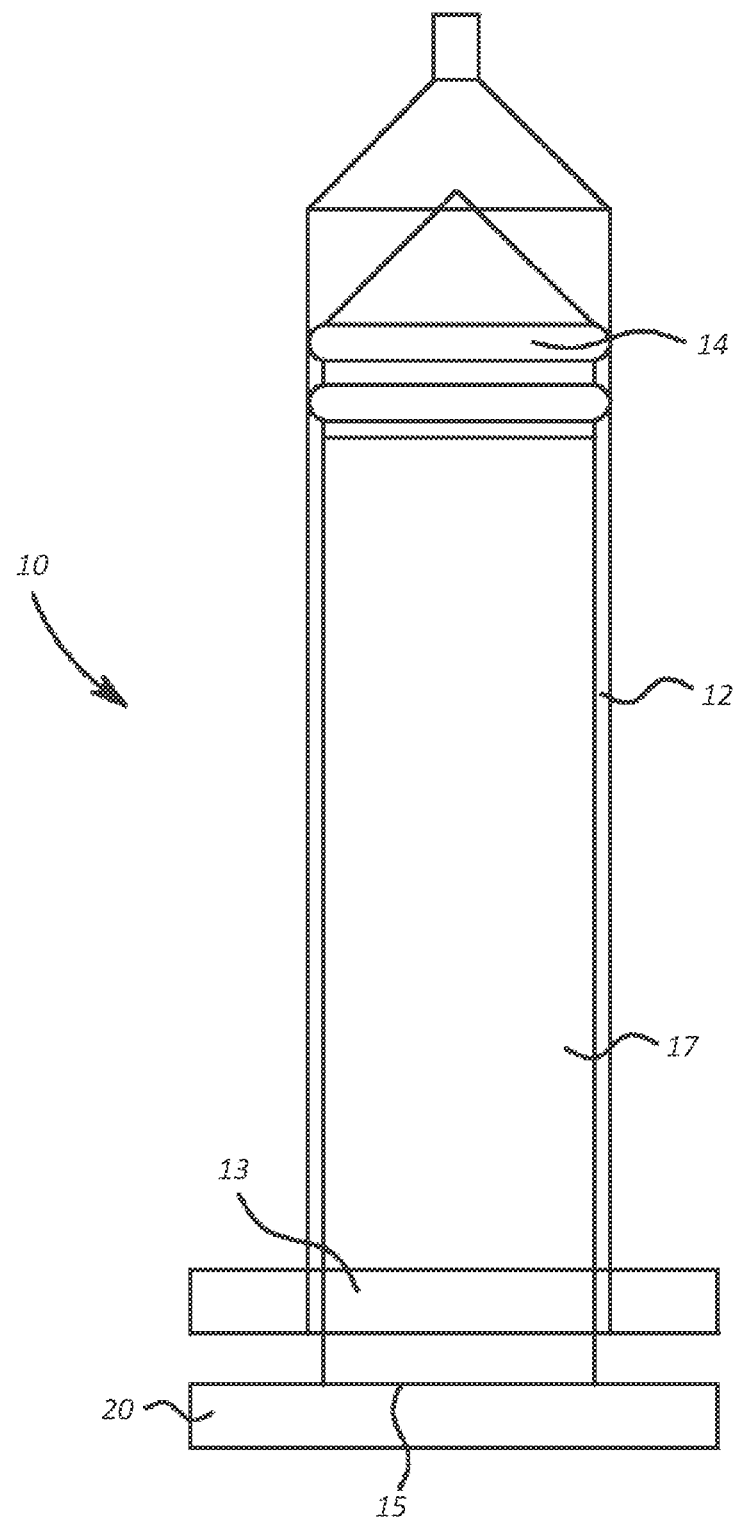
FIG. 1 is a side view of a syringe, according to one aspect of the present disclosure.

Various forms are directed to syringe plungers with dynamic seals to provide enhanced sealing during injection procedures under injection pressure conditions. With reference to FIG. 1, in one aspect, a syringe 10 includes a barrel 12, a plunger 14, and a plunger rod 17. The plunger 14 is slideably inserted in the barrel 12. The plunger 14 may be removable or non-removeably or integrally connected to the plunger rod 17. A proximal end 15 of the plunger rod 17 extends outward from a proximal end 13 of the barrel 12 and is configured to form an interface with an external piston (not shown) configured to be driven by a fluid injector, such as a powered or automatic injector. The interface between the plunger rod 17 of the syringe 10 and an external piston may include a connecting surface structure, such as a mating element 20, extending from the proximal end 15 of the plunger rod 17. The mating element 20 is configured to engage with the external piston. The external piston may include a piston rod (not shown). In alternate aspects, plunger 14 may directly interface with the external piston.

In use, the external piston is brought into contact with the mating element 20 of the syringe 10 and engages the mating element 20. In one aspect, the syringe may be disposable. Various techniques may be employed to engage the external piston with the mating element 20. Once engagement is established, the external piston can be retracted to fill the syringe 10 with fluid or driven in the proximal direction to eject fluid contained therein. Once the fluid is ejected, a slider (not shown) is moved in the proximal direction to disengage the external piston from the mating element 20. Once disengaged, a user can dispose of the syringe 10. Additional examples of syringes can be found in commonly assigned US Publication No. 2016/0151570, filed Jul. 9, 2014, and titled VACUUM SYSTEM FOR SYRINGE INTERFACE, U.S. Pat. Nos. 9,173,995; 9,199,033; and 9,700,670, and U.S. application Ser. No. 15/541,573, the disclosures of which are incorporated herein by reference.

Figure 2:
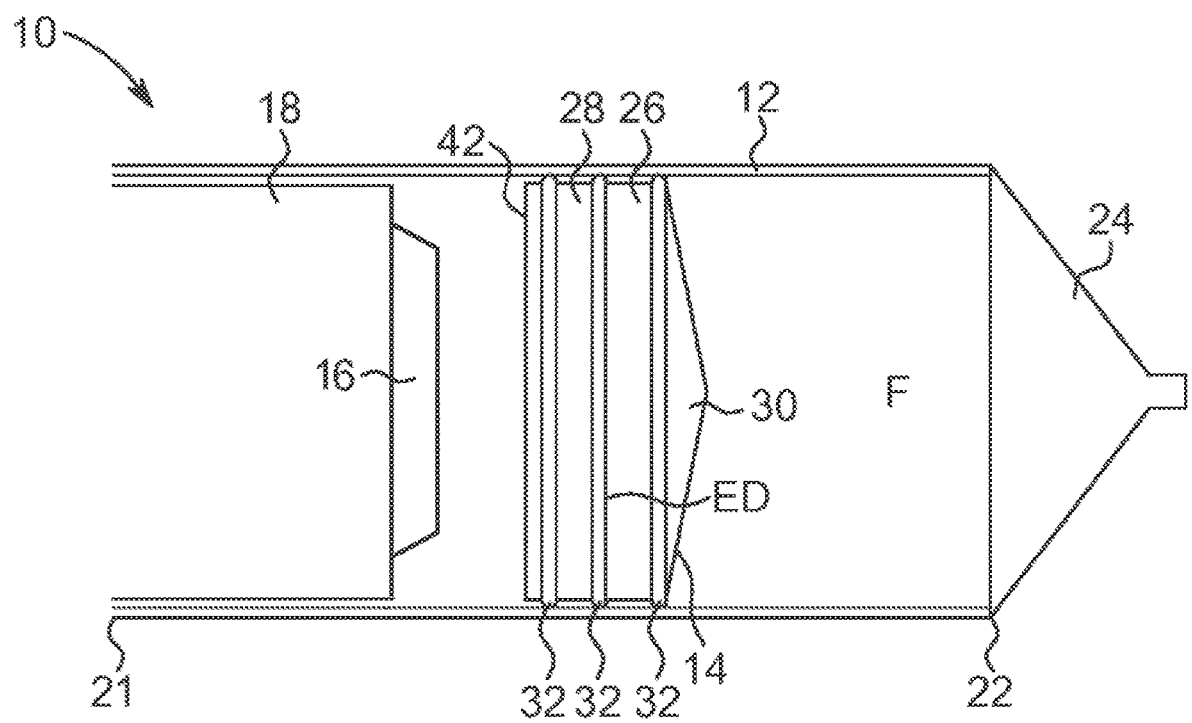
FIG. 2 is a schematic cross-sectional view of a syringe interface having a piston and plunger, according to one aspect of the present disclosure.

Referring to FIG. 2, the syringe 10 includes a barrel 12 that may be cylindrical, and a plunger 14, as well as a method of pushing and retracting the plunger 14 through the barrel 12 as described in connection with FIG. 1. The syringe 10 generally includes the barrel 12, a plunger 14, and a piston 18 for advancing and retracting the plunger 14 through the barrel 12. The piston 18 may include a piston head 16 for engaging the plunger 14. The piston 18 optionally may include a handle (not shown) allowing a user to manually advance the plunger 14. Alternatively, the piston 18 is connected to a mechanical mechanism, such as a powered injector, powered linear actuator, or fluid injector, for automatically driving the piston head 16 and plunger 14 through the barrel 12. The piston 18 can be made of a rigid plastic. Examples of piston to plunger engagement mechanisms may be found, for example, in U.S. Pat. Nos. 9,480,797 and 7,666,169, the disclosures of which are incorporated herein by reference.

The barrel 12 is adapted to contain a fluid F, such as a medicament, biological solution, saline, or contrast agent, to be injected to a patient. The barrel 12 extends longitudinally from a proximal end 21, near the injector apparatus, to a distal end 22 and is configured to expel the fluid F from the distal end 22 of the barrel 12. The distal end 22 may include an outflow port 24, such as a nozzle, needle cannula, or catheter tubing. The barrel 12 may be formed from any suitable biocompatible and medical grade material including glass, metal, ceramic, plastic, rubber, or combinations thereof.

The plunger 14 is adapted to be slidably inserted in the barrel 12, and includes a cylindrical body 26 formed of elastomeric material, a sidewall 28, and a conical cap 30. The plunger 14 has an external diameter ED that corresponds to an inner diameter ID of the barrel 12, such that a fluid seal is formed between the sidewall 28 and an inner wall 29 of the barrel 12. In certain aspects, the sidewall 28 includes one or more annular ribs 32 extending radially from the sidewall 28. The annular ribs 32 are adapted to contact and compress against the inner wall 29 to form a fluid tight seal and are adapted to slide against the inner wall 29 of the barrel 12 as the plunger 14 is advanced or retracted while maintaining the fluid tight seal. The annular ribs 32 reduce the contact surface area against the inner wall 29 of the barrel 12, which lessens the frictional forces between the barrel 12 and plunger 14 and allows the plunger 14 to slide through the barrel 12 more easily.

The plunger 14 may further include an annular shoulder 42 or ring positioned on a proximal end of the plunger 14. The annular shoulder 42 contacts a corresponding portion of the piston 18 or piston head 16 for imparting additional pushing force against the plunger 14.

The sidewall 28 is flexible and can deform outwards to increase the size of the opening and cavity defined by an inner portion of the plunger 14, to accept the piston head 16 and/or support ring 116. In certain aspects, a portion of the sidewall 28 may essentially be hollow and include an annular channel (not shown) to reduce the structural integrity of the sidewalls 28, thereby further increasing the flexibility.

In use, the piston head 16 is inserted into the cavity defined by the plunger 14 establishing a removable engagement therebetween. The engagement is sufficient to maintain the connection between the plunger 14 and piston head 16 both as the plunger 14 is advanced through and retracted from the barrel 12. As such, the engagement must be strong enough to counteract both the initial frictional breakaway force created by the contact between the sidewall 28 and/or annular ribs 32 of the plunger 14 and the inner surface of the barrel 12, as well as the dynamic frictional forces created as the plunger 14 slides through the barrel 12 and at least partial vacuum that is created as plunger 14 is retracted to draw liquid F into the syringe.

Figure 3:
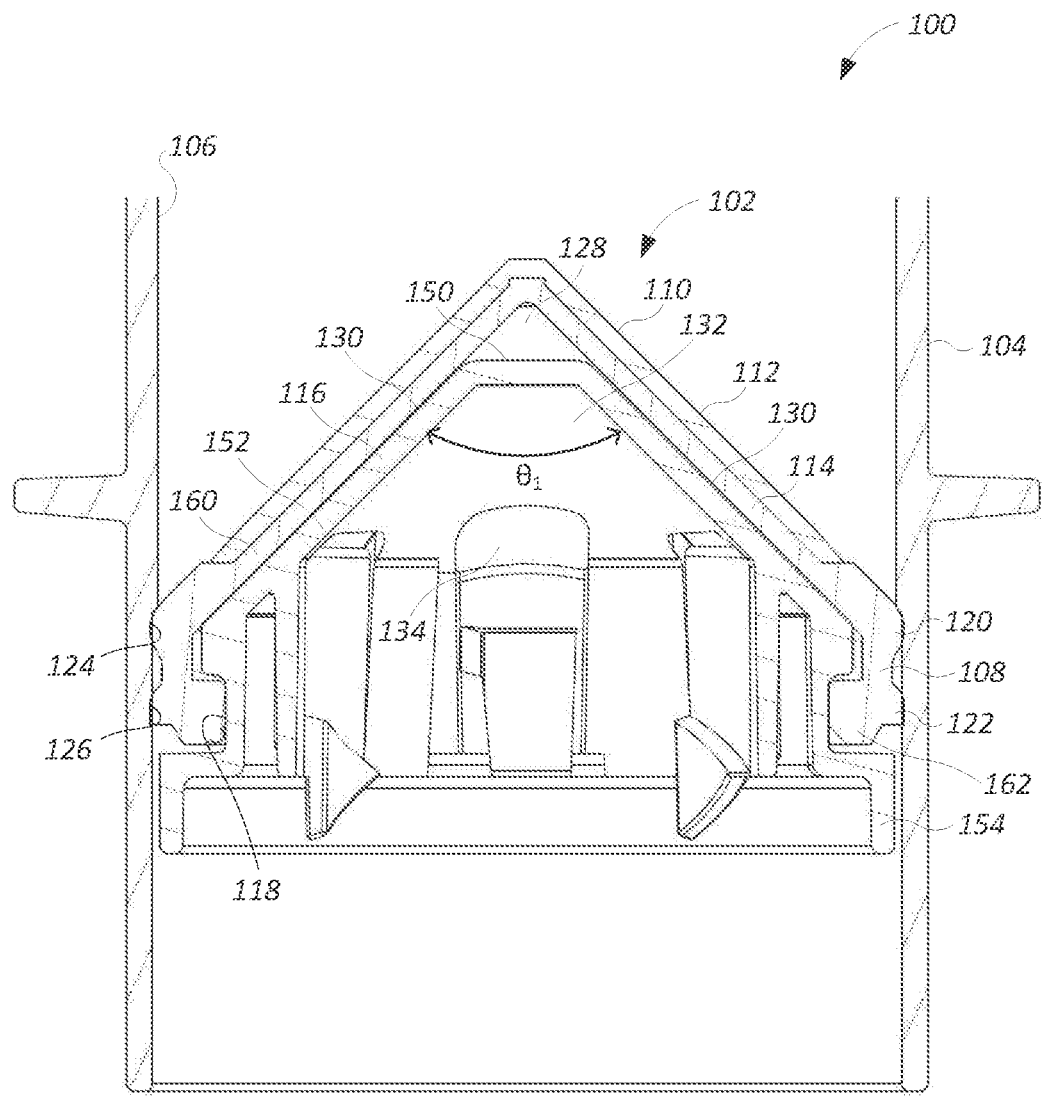
FIG. 3 is a sectional view of a syringe plunger system, according to one aspect of the present disclosure.

FIG. 3 is a sectional view of a syringe plunger system 100 according to one aspect. The syringe plunger system 100 includes an included angle $\theta_1$ about 90°, for example from 85° to 95°. As used herein the term "about" when referencing an angle of the plunger system means plus or minus 5°. The syringe plunger system 100 includes a plunger 102 disposed within a barrel 104 of the syringe. The barrel 104 defines an inner wall 106 configured to slideably receive the plunger 102. The plunger 102 includes a support ring 116, a cover 114 disposed and snap fit over the support ring 116, and a conical cap 110 disposed over the cover 114. When the plunger 102 is under injection pressure conditions, the plunger 102 is axially deflected and the cover 114 is radially deflected towards the inner wall 106 of the barrel 104 to provide greater seal under injection pressure conditions. In certain aspects, the conical cap 110 may include an overmold element 112.

The cover 114 includes a cylindrical sidewall 108, a conical cap 160, and a flange 162 such as a projecting rim or edge for coupling the cover 114 to the support ring 116. The cover 114 includes one or more annular ribs, such as a first annular rib 120 and a second annular rib 122. The first annular rib 120 is received in a first annular slot 124 defined by the inner wall 106 of the barrel 104 and the second annular rib 122 is received in an annular slot 126 also defined by the inner wall 106 of the barrel 104.

The support ring 116 includes an annular shoulder 154, a conical cap 152, and an annular groove 118 defined therebetween to receive the flange 162 of the cover 114. The conical cap 152 of the support ring 116 defines an included angle $\theta_1$ of about 90° and an annular groove 118 to receive the cover 114 portion of the conical cap 110. The support ring 116 defines an inner volume 132 within the conical cap 160. At least one aperture 134 is defined by the support ring 116 to provide an exit path for the air between the cover 114 and the support ring 116 during injection pressurization. The air is vented through the at least one aperture 134 back outside of the barrel 104 of the syringe and away from the path of the fluid.

An air cavity 128 is defined between the tip 150 of the conical cap 152 of the support ring 116 and the conical cap 160 of the cover 114. The conical cap 160 of the cover 114 is in contact with and supported by the conical cap 152 of the support ring 116 at an interface 130. There is no a gap or air cavity defined at the interface 130.

Figure 4:
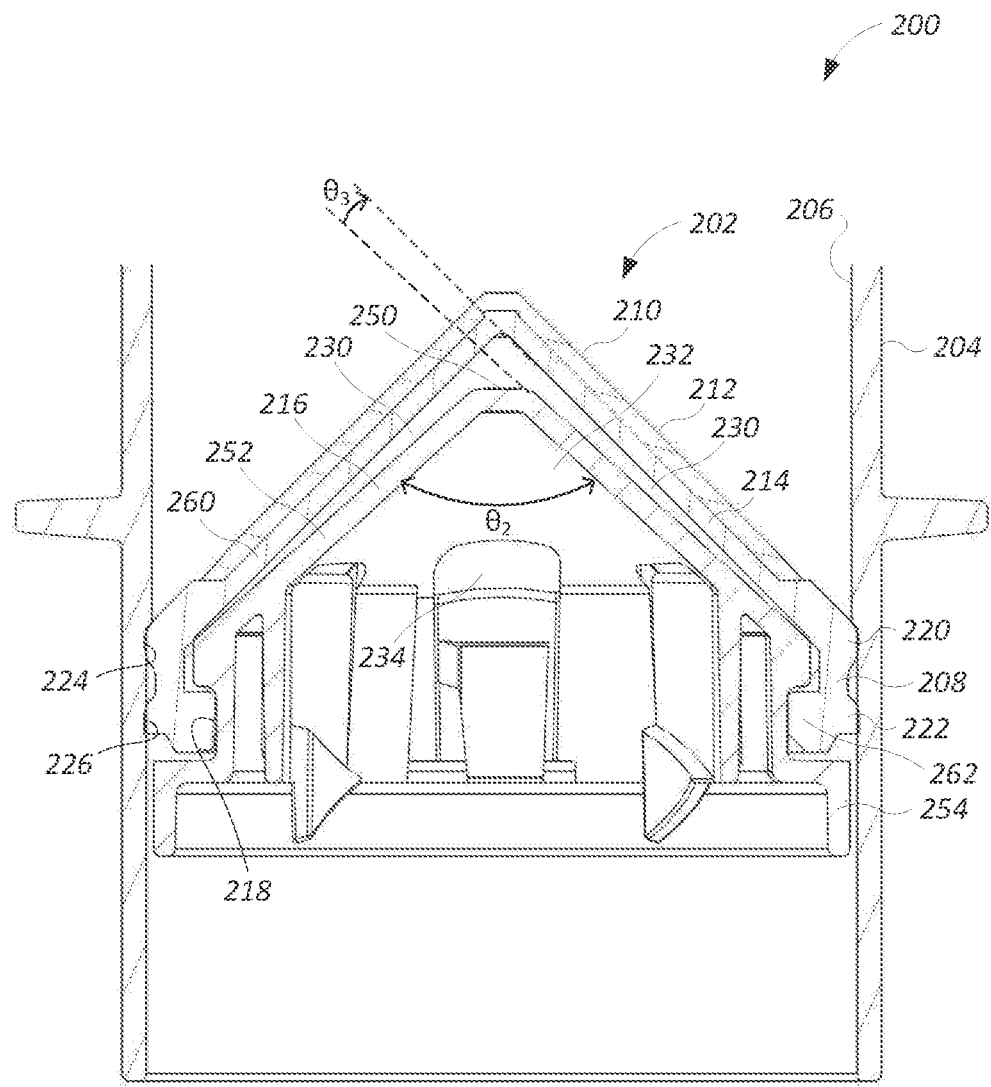
FIG. 4 is a section view of one aspect of a syringe plunger system with a dynamic seal, according to one aspect of the present disclosure.

FIG. 4 is a sectional view of a syringe plunger system 200 with a dynamic seal according to another aspect. The syringe plunger system 200 is shown prior to injection pressurization. The syringe plunger system 200 includes an included angle $\theta_2$ greater than about 90°. As will be described hereinbelow, an increase in the included angle $\theta_2$ above about 90° increases the sealing pressure limits of the syringe plunger system 200. Alternatively, the syringe plunger system 200 includes an included angle $\theta_2$ of about 90° on the conical cap 252 of the support ring 216 and an included angle of less than about 90° on the conical cap 260 of the of the cover 214. The syringe plunger system 200 includes a plunger 202 disposed within a syringe barrel 204 of the syringe. The syringe barrel 204 defines an inner wall 206 configured to slideably receive the plunger 202. The plunger 202 includes a support ring 216, a cover 214 disposed over and coupled to the support ring 216, and a conical cap 210 disposed over the cover 214. In one aspect, the cover 214 may be snap fit to the support ring 216. When the plunger 202 is under injection pressure conditions, the plunger 202 is axially deflected and the cover 214 is radially deflected towards the inner wall 206 of the syringe barrel 204 to provide a greater seal under injection pressure conditions. The conical cap 210 may include an overmold element 212.

The cover 214 includes a cylindrical sidewall 208, a conical cap 260, and a flange 262 such as a projecting rim or edge for coupling the cover 214 to the support ring 216. The cover 214 includes a first annular rib 220 and a second annular rib 222. The first annular rib 220 is received in a first annular slot 224 defined by the inner wall 206 of the syringe barrel 204 and the second annular rib 222 is received in a second annular slot 226 also defined by the inner wall 206 of the syringe barrel 204.

The support ring 216 includes an annular shoulder 254, a conical cap 252, and an annular groove 218 defined therebetween to receive the flange 262 of the cover 214. The conical cap 252 of the support ring 216 defines an included angle $\theta_2$ greater than about 90° and an annular groove 218 to receive the cover 214 portion of the conical cap 210. In the illustrated example, the included angle $\theta_2$ is 96°, although the disclosure is not limited in this context, as the included angle $\theta_2$ can be calculated to produce an optimal effect of the dynamic seal. The support ring 216 defines an inner volume 232 within the conical cap 252. At least one aperture 234 is defined by the support ring 216 to provide an exit path for the air between the cover 214 and the support ring 216 during injection pressurization. The air is vented through the at least one aperture 234 back outside of the syringe barrel 204 of the syringe and away from the path of the fluid.

The conical cap 252 of the support ring 216 and the conical cap 260 of the cover define a gap or air cavity 230 therebetween. The air cavity 230 or "gap" is defined between the support ring 216 and the cover 214 along the conical portion of the plunger 202. An angle $\theta_3$ is defined between the support ring 216 and the cover 214 and defines the air cavity 230. The angle $\theta_3$ can vary from a value greater than 0° to less than about 30°, for example, and nominally is about 6°. The air cavity 230 defines a predetermined compliance volume such that when the syringe plunger system 200 undergoes injection pressurization, the overmold element 212 and the cover 214 deform and flex into the compliance volume defined by the air cavity 230. The injection pressure applies an axial force to the overmold element 212 and the cover 214 causing them to deform and compress the air cavity 230, which applies a radial force to the first and second annular ribs 220, 222 to engage the respective first and second annular slots 224, 226 and/or against the side wall 206 to create a dynamic seal under injection pressure conditions. The volume of the air cavity 230 increases as the included angle $\theta_2$ is increased. The volume of the air cavity 230 can be optimized by suitable selection of the included angle $\theta_2$. Thus, the compliance volume can be increased or decreased based on the included angle $\theta_2$. The included angle $\theta_2$ can vary from a value greater than about 90° to less than about 120°, for example, and nominally is about 96°. The compliance volume can vary from about 0.1 mL to 10 mL, for example. With an included angle $\theta_2$ of about 96°, as shown in FIG. 4, the compliance volume is about 1 mL. The size of the air cavity 230 or "gap" translates to sealing pressure of the dynamic seal. The optimal size of the air cavity 230 can be calculated to produce an optimal dynamic seal for a particular injector/syringe application. This optimal effect may be equivalent to a maximum added compression for sealing, for example.

While the term "air cavity" is used herein to describe the compressible volume between the conical cap 252 of the support ring 216 and the conical cap 260 of the cover, other compressible materials may also be included in the volume between the conical cap 252 of the support ring 216 and the conical cap 260 of the cover. For example, in certain aspects, the volume between conical cap 252 and conical cap 260 may be filled with a bladder containing a compressible fluid, for example a compressible gas or other fluid. In another aspect, the volume between conical cap 252 and conical cap 260 may be filled with a compressible material, such as an elastic material with a low modulus that can deform under the pressure loads associated with an injection procedure. Non-limiting examples may include a compressible or deformable material, such as thermoplastic elastomer or a foam material, which compresses to allow for a dynamic seal under pressure loads typical of an injection procedure. In certain aspects, predictable compression and thereby, predictable control of the dynamic seal between the plunger side wall and the interior wall of the syringe may be achieved by selecting a material having a certain strain or compression factor under a desired pressure load. In certain aspects, the compression of the material would reverse in the absence of the pressure load of the injection procedure.

In one aspect the body of the syringe barrel 204 can be made of polyethylene terephthalate commonly abbreviated PET such as Eastman MN052 PET, for example. The support ring 216 can be made of a polycarbonates (PC) thermoplastic polymer or any suitable medical grade polymer that is strong, tough, and may be optically transparent and can be easily worked, molded, and thermoformed, such as Lexan 141, for example. The cover 214 may be made of a thermoplastic elastomer (TPE), sometimes referred to as thermoplastic rubbers, or other mix of polymers such as plastic and a rubber with both thermoplastic and elastomeric properties, such as Santoprene 181-5, for example. The cover 214 may be optically transparent or translucent. Thermoplastics may be desirable due to their relatively easy of use in manufacturing and ability of being injected molded. The overmold element 212 may be made of polypropylene (PP), also known as polypropylene thermoplastic polymer, such as polypropylene P5M4K-046, for example, and may be optically transparent or translucent. The syringe barrel 204, the support ring 216, the cover 214, and the overmold element 212 are made of medical grade plastics and materials.

Figure 5A:
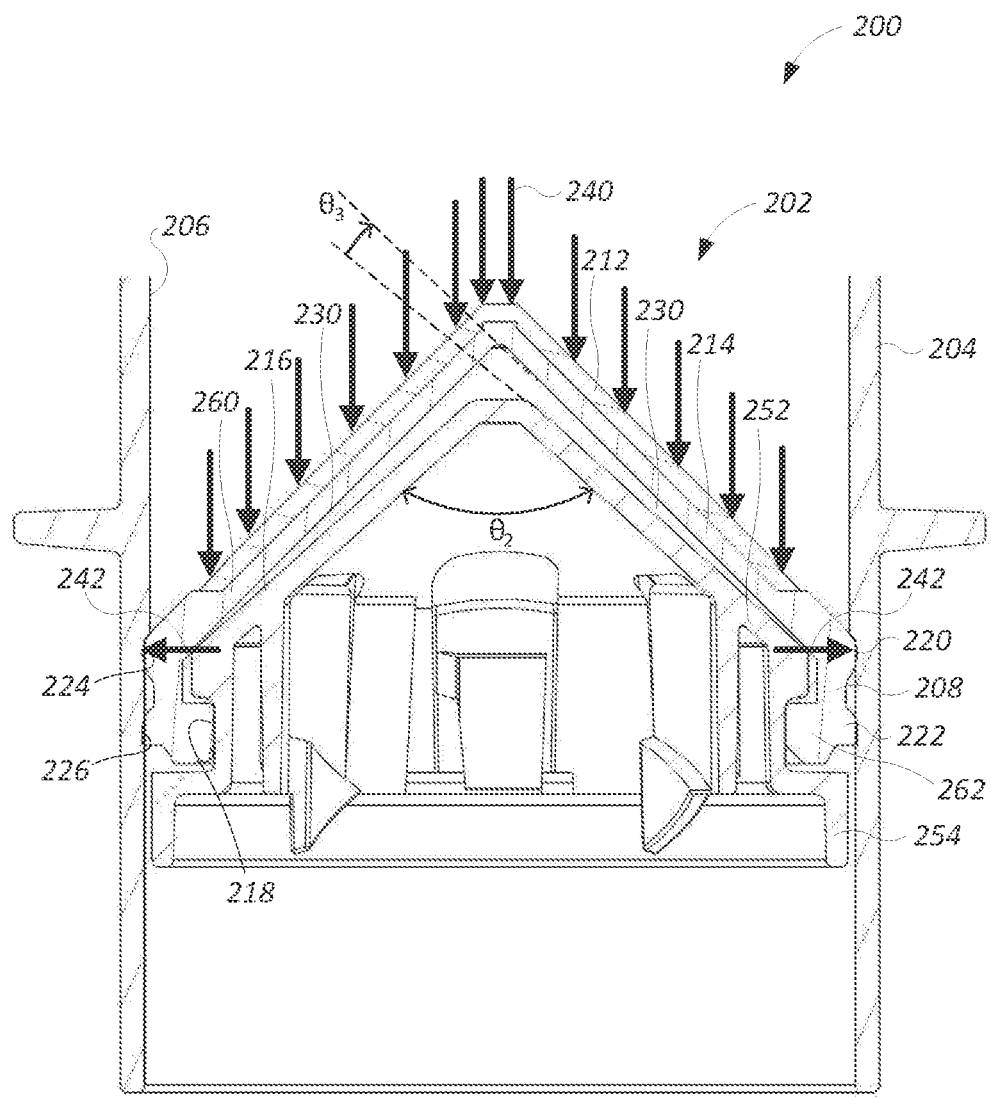
FIG. 5A is a section view of one aspect of the syringe plunger system with a dynamic seal shown in FIG. 4 in an initial compression state, according to one aspect of the present disclosure.
Figure 16:
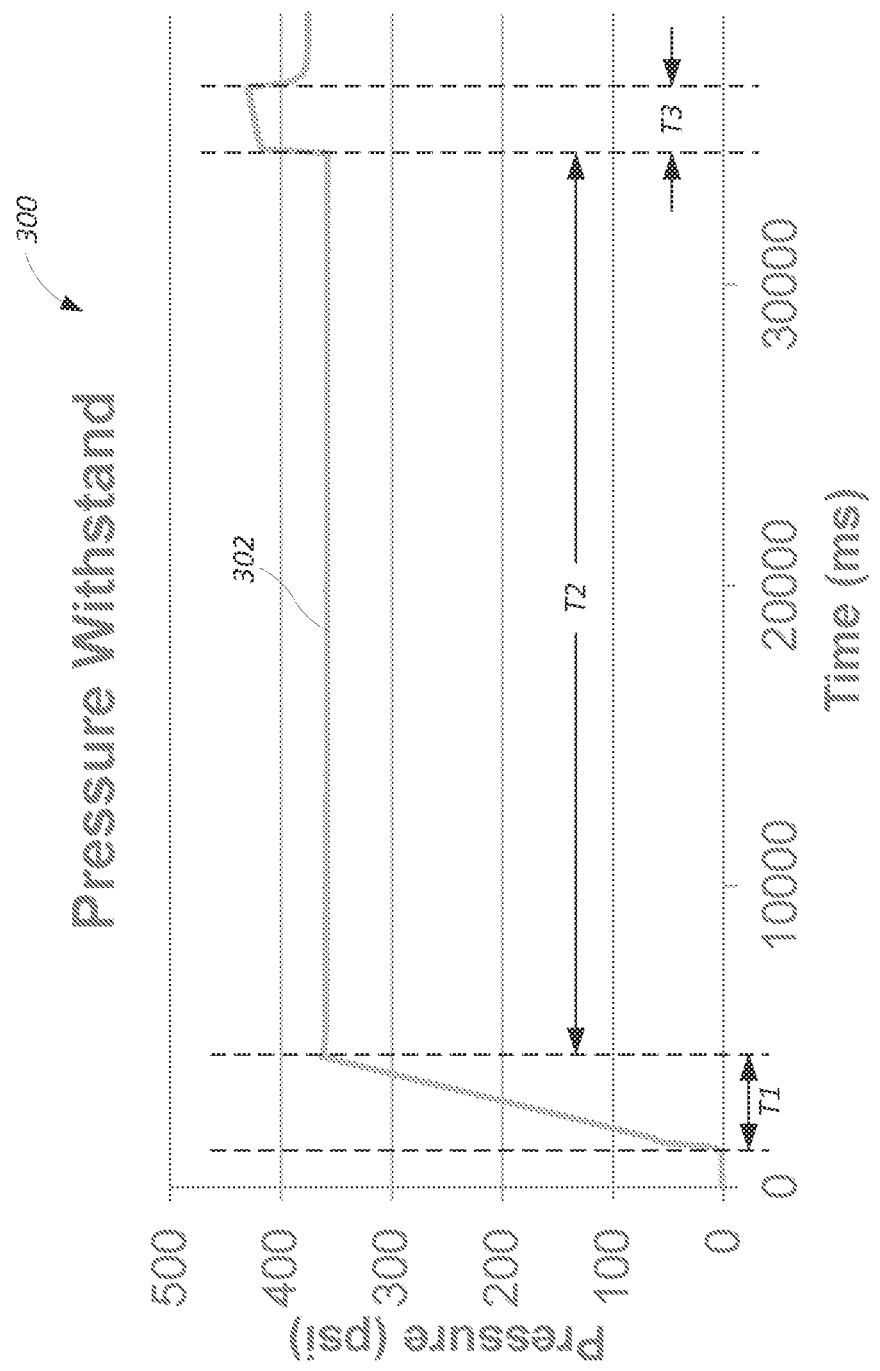
FIG. 16 is a graphical representation of the maximum pressure that the syringe plunger system described in connection with FIGS. 4-15 withstands after a sustained period of pressurization, according to one aspect of the present disclosure.

FIG. 5A is a section view of one aspect of the syringe plunger system 200 with a dynamic seal shown in FIG. 4 in an initial compression state. In the example illustrated in FIG. 5A, the included angle $\theta_2$ is about 96°. Nevertheless, as described in connect ion with FIG. 4, the included angle $\theta_2$ may be varied to optimize the dynamic seal. The compliance volume defined by the air cavity 230 is an initial compression state upon the initial application of injection pressure 240, represented by the vertical arrows, and causes axial deflection of the plunger 202 in the direction indicated by the vertical arrows. The injection pressure 240 applied to the overmold element 212 causes the cover 214 to deform or change shape. The change in shape of the cover 214 applies a radial force 242, represented by the horizontal arrows, and causes radial deflection of the plunger 202 in the direction indicated by the horizontal arrows, against the inner wall 206 of the syringe barrel 204 to provide greater seal pressure. The radial force 242 pushes the first and second annular ribs 220, 222 into the respective first and second annular slots 224, 226 to create a dynamic seal against the inner wall 206 of the syringe barrel 204. Accordingly, the seal force between the plunger 202 and the inner wall 206 of the syringe barrel 204 is a dynamic function of the injection pressure 240. Accordingly, syringe barrel 204 swell due to creep is managed since the higher seal force is present only for short durations of time during injections. This function can be employed to define a pressure withstand requirement for the syringe plunger system 200 of injection pressure (PSI) versus time (mS). In one aspect, the syringe plunger system 200 can withstand injection pressures greater than or equal to 355 psi for 30 seconds and can withstand injection pressures greater than or equal to 405 psi for 1 second, as shown in FIG. 16, for example. Elasticity of the plunger 202 enhances the importance of the dynamic seal. Pressure ranges include 0 to 2000 PSI depending on material and type of injection (e.g., CT or CV). For CT injection, maximum injection pressure is about 500 PSI and nominal operating pressure is about 150-350 PSI. For CV injection, maximum injection pressure is about 1500 PSI and nominal operating pressure is about 300-800 PSI.

Figure 5B:
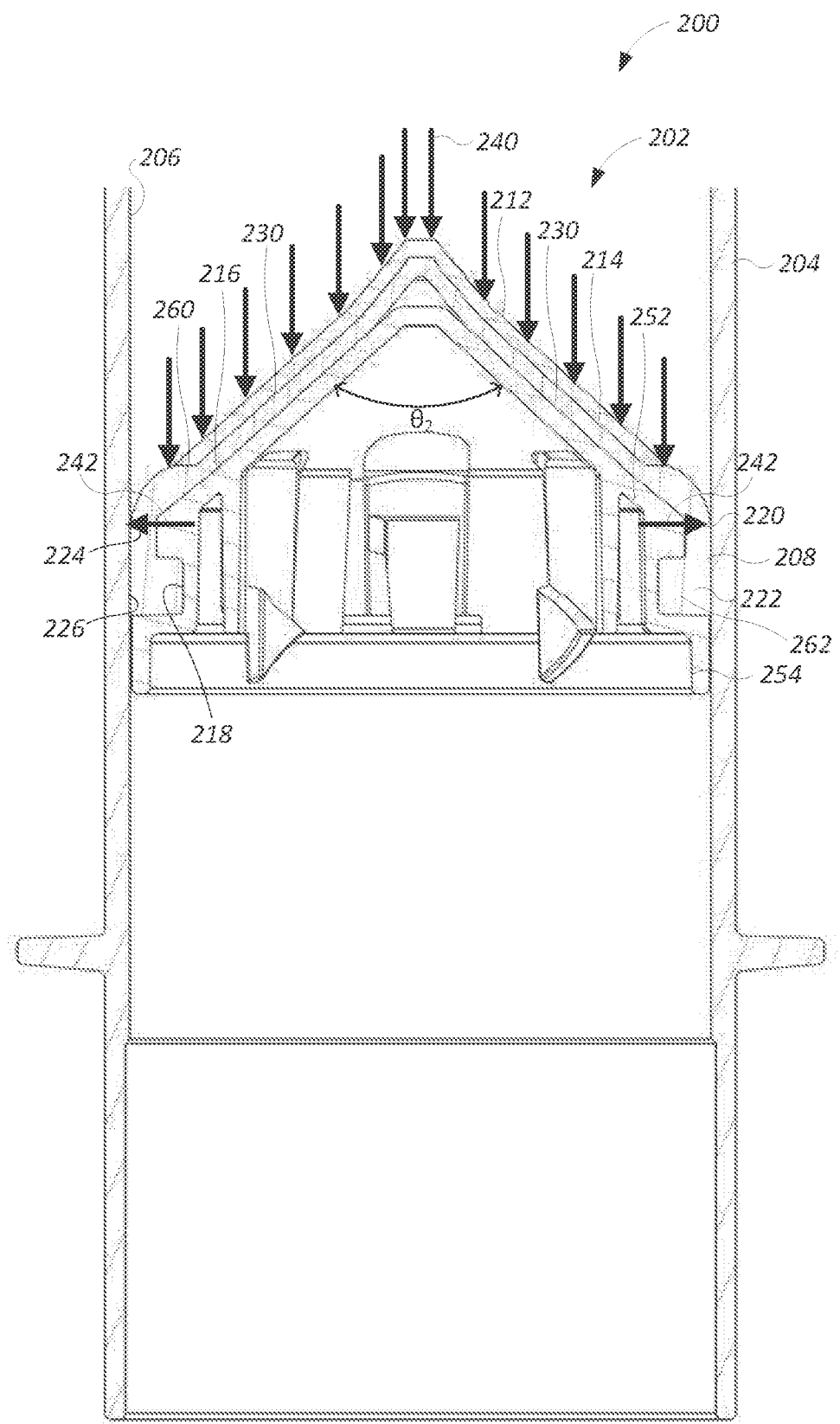
FIG. 5B is a section view of one aspect of the syringe plunger system with a dynamic seal shown in FIG. 5A in a compressed state, according to one aspect of the present disclosure.

FIG. 5B is a section view of one aspect of the syringe plunger system 200 with a dynamic seal shown in FIG. 5A in a compressed state. As shown, the injection pressure 240 applied to the overmold element 212 causes the cover 214 to deform or change shape. The change in shape of the cover 214 applies a radial force 242, represented by the horizontal arrows, and causes radial deflection of the plunger 202 in the direction indicated by the horizontal arrows, against the inner wall 206 of the syringe barrel 204 to provide greater seal pressure. The radial force 242 pushes the first and second annular ribs 220, 222 into the respective first and second annular slots 224, 226 and/or against the side wall 206 to create a dynamic seal against the inner wall 206 of the syringe barrel 204.

Figure 6:
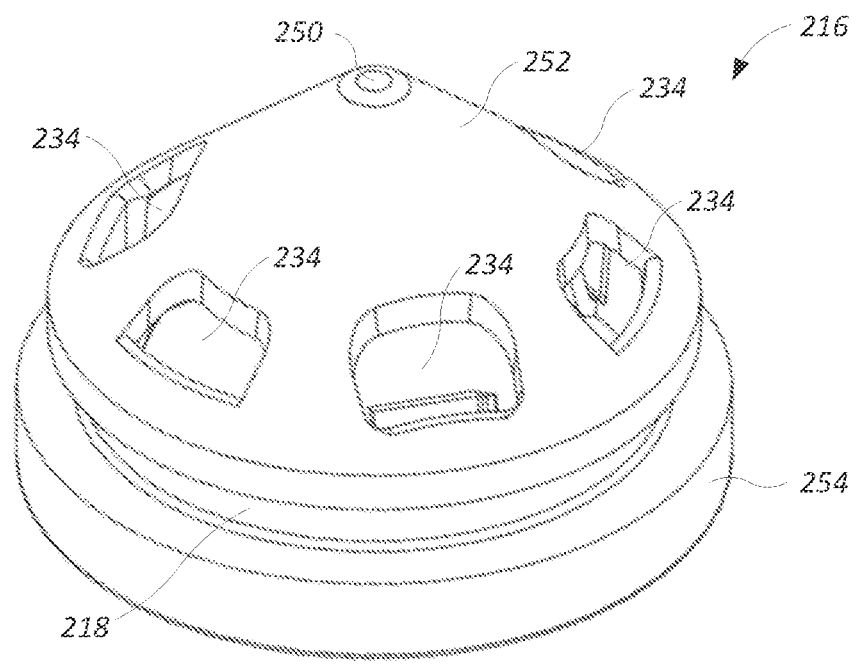
FIGS. 6-11 illustrate several views of a support ring structure that includes an included angle, where.
Figure 7:
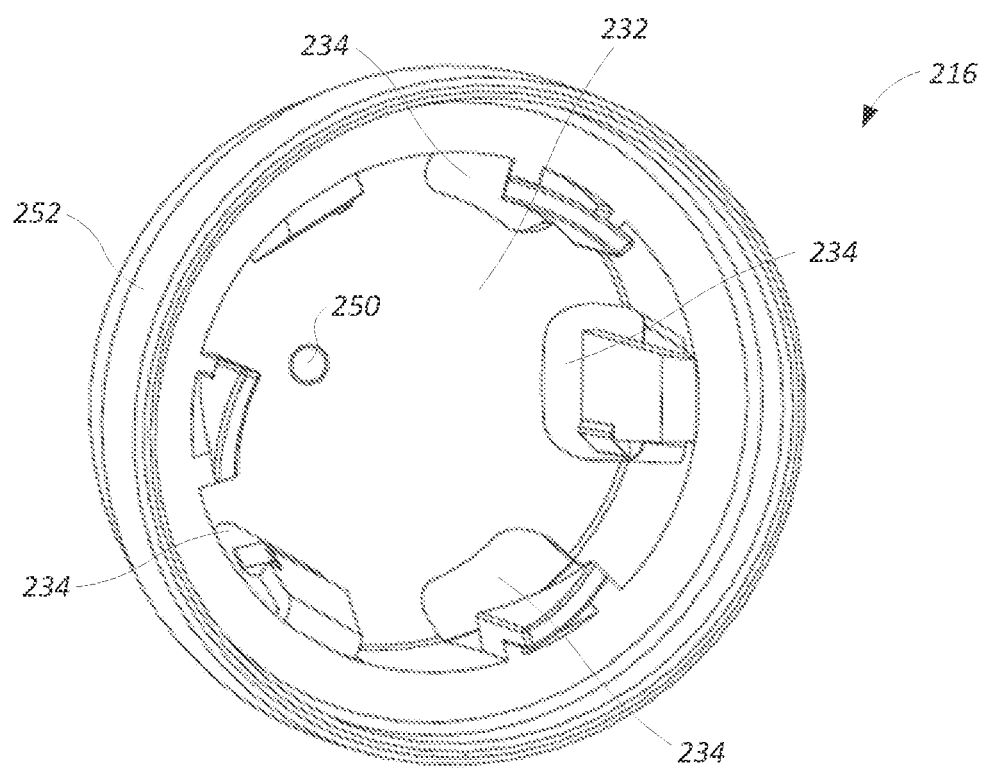
Figure 8:
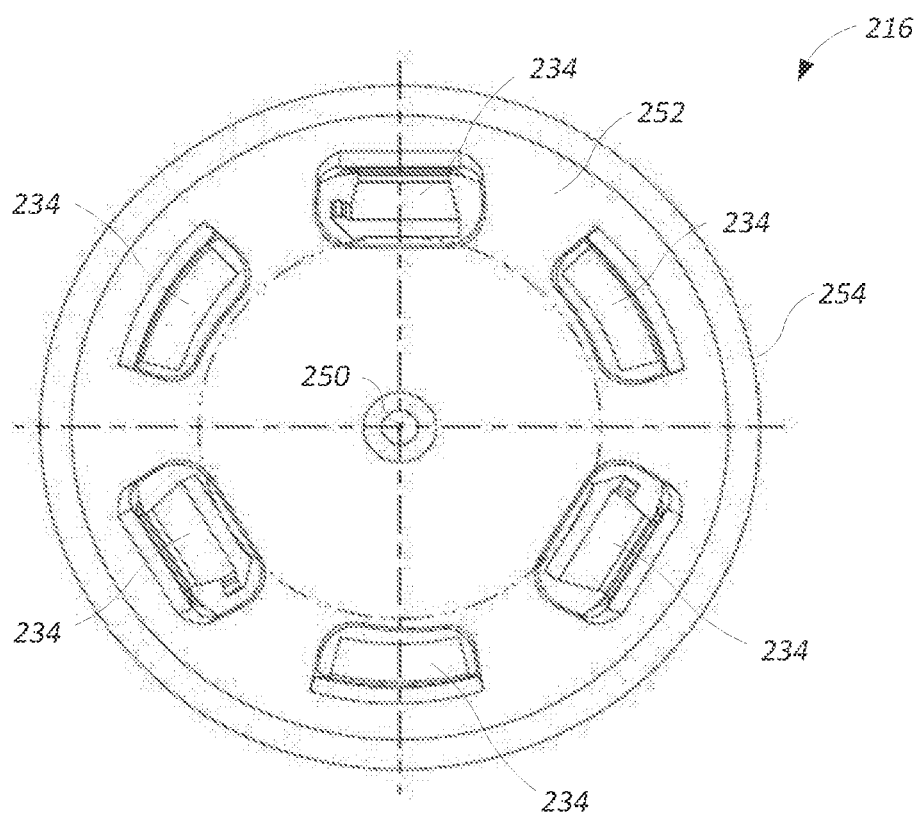
Figure 9:
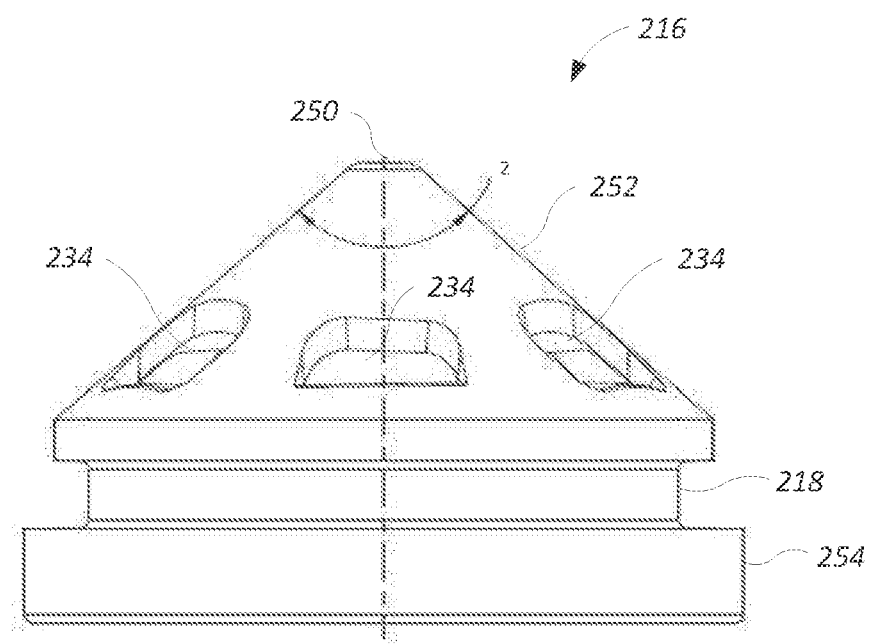
Figure 10:
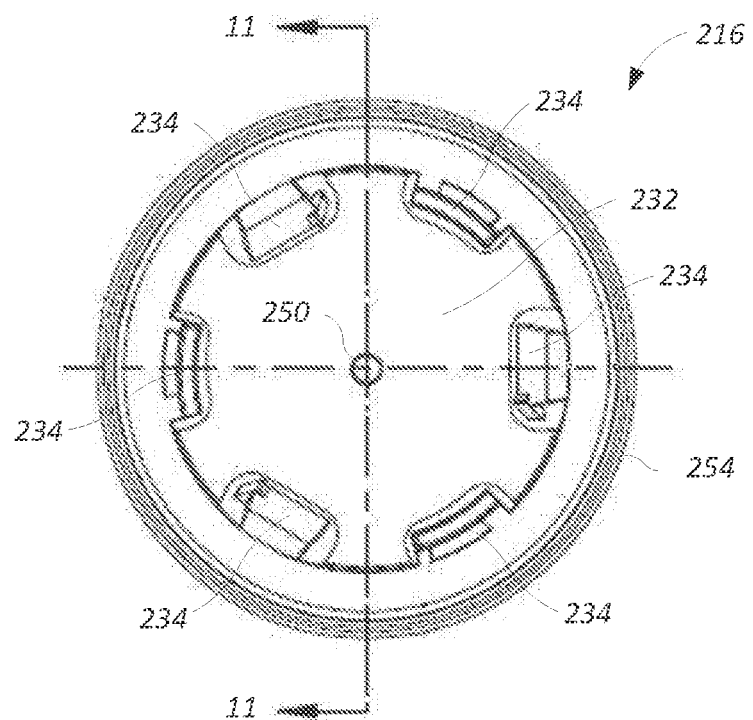
Figure 11:
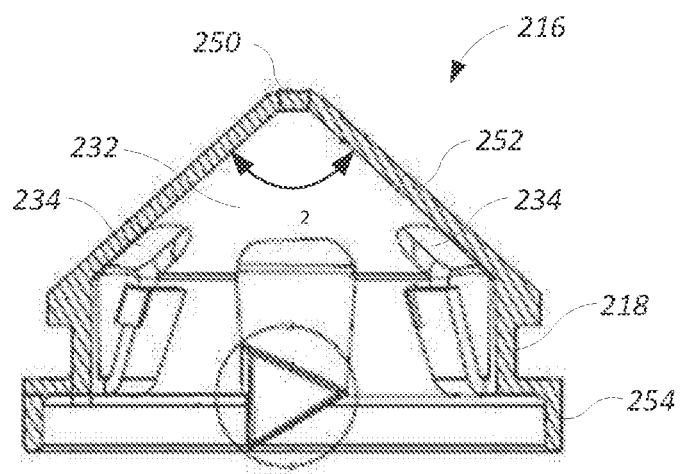

FIGS. 6-11 illustrate several views of one aspect of a support ring 216 structure that includes a conical cap 252 that defines an included angle $\theta_2$. Further details of support rings such as 216 may be found in U.S. Pat. Nos. 7,666,169; and 9,480,797, incorporated by reference herein. FIGS. 6 and 7 are perspective views of the support ring 216. FIG. 8 is a plan view of the support ring 216. FIG. 9 is an elevational view of the support ring 216. FIG. 10 is a bottom view of the support ring 216 and FIG. 11 is a sectional view of the support ring 216 taken along section line 11-11 as shown in FIG. 10. With reference to FIGS. 6-10, the support ring 216 includes a tip 250, a conical cap 252, and an annular shoulder 254. The conical cap 252 defines an included angle $\theta_2$ that is greater than about 90° and less than about 120°. In the illustrated example, the included angle $\theta_2$ is about 96°, although the include angle $\theta_2$ may be optimized to achieve a predetermined dynamic seal force between the plunger 202 and the barrel (FIGS. 4 and 5A, B). The conical cap 252 may define a one or more or even a plurality of apertures 234 to vent air back outside the syringe barrel 204 and away from the fluid path. An annular groove 218 is defined between the conical cap 252 and the annular shoulder 254. The annular groove 218 is configured to snap fit receive the cover 214 (FIGS. 4 and 5A, B). The conical cap 252 of the support ring 216 defines an inner volume 232. While one embodiment of the support ring 216 is illustrated in FIGS. 6-11, other embodiments and configurations of support ring 216 are considered, for example support rings with different piston engagement mechanisms (such as described in U.S. Pat. No. 7,666,169) and/or with configurations having no apertures 234 in the conical cap 252 or, alternatively having one aperature 234. In aspects having no apertures 234 in the conical cap 252, compression during an injection procedure may compress the air in the air cavity 230 or, alternatively force the air in the air cavity 230 out between the plunger cover 214 and the support ring 216.

Figure 12:
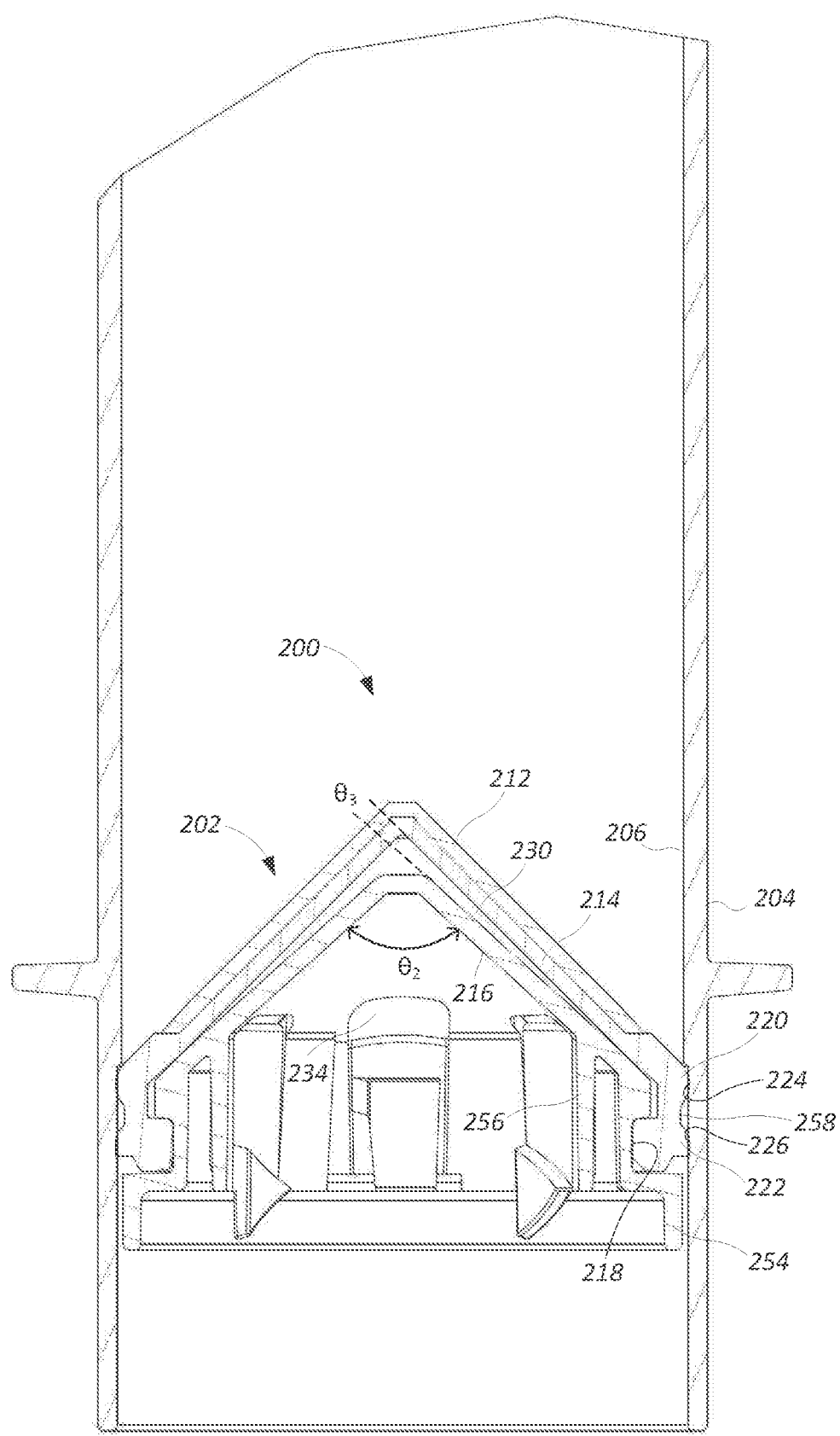
FIG. 12 is a sectional view of the syringe plunger system with dynamic seal in a shipping configuration, according to one aspect of the present disclosure.

FIG. 12 is a sectional view of the syringe plunger system 200 with a dynamic seal in a shipping configuration. In the shipping configuration, the plunger 202 is under a pressure that is significantly lower than a nominal injection pressure. The syringe plunger system 200 includes a syringe barrel 204 defining an inner wall 206 and a plunger 202 disposed within the syringe barrel 204. The plunger 202 includes a support ring 216 that defines an included angle $\theta_2$ that is greater than about 90°, and in one example is approximately about 96°. As previously described, the included angle $\theta_2$ may have a value between about 90° and about 120°, for example. The support ring 216 includes engagement features for reversible engagement with a piston of a medical injector, which reciprocates the plunger 202 within the syringe barrel 204. The support ring 216 defines at least one aperture 234 to vent air back outside of the syringe barrel 204 and away from the fluid path. The plunger 202 further includes a cover 214 that is configured to snap fit over the support ring 216 into the annular groove 218 defined by the support ring 216. The cover 214 also includes first and second annular ribs 220, 222 configured to be received within respective first and second annular slots 224, 226 defined in the inner wall 206 of the syringe barrel 204 to form a dynamic seal under injection pressure conditions. An overmold element 212 may be disposed over the cover 214.

As shown in FIG. 12, an angle $\theta_3$ is defined between the support ring 216 and the cover 214 to define an air cavity 230 therebetween. The air cavity 230 defines a predetermined compliance volume such that when the syringe plunger system 200 in under injection pressure, the cover 214 and the overmold element 212 are subjected to axial forces and flexibly distort to compress the compliance volume defined by the air cavity 230. Under injection pressure conditions, the distortion applies a radial force to push the first and second annular ribs 220, 222 into the respective first and second annular slots 224, 226 and/or against the side wall 206 of the syringe barrel to form primary and secondary dynamic seals, respectively. As previously discussed, the air cavity 230 may be configured to define a predetermined volume ranging from 0.1 mL to 10 mL. A gap 258 is defined between the support ring 216 and the inner wall 206 of the syringe barrel 204 when the plunger 202 is in a shipping configuration and not under injection pressure. Configurations of the syringe plunger system 200 shown in FIG. 12 under various states of compression are described hereinbelow in connection with FIGS. 13-15.

Figure 13:
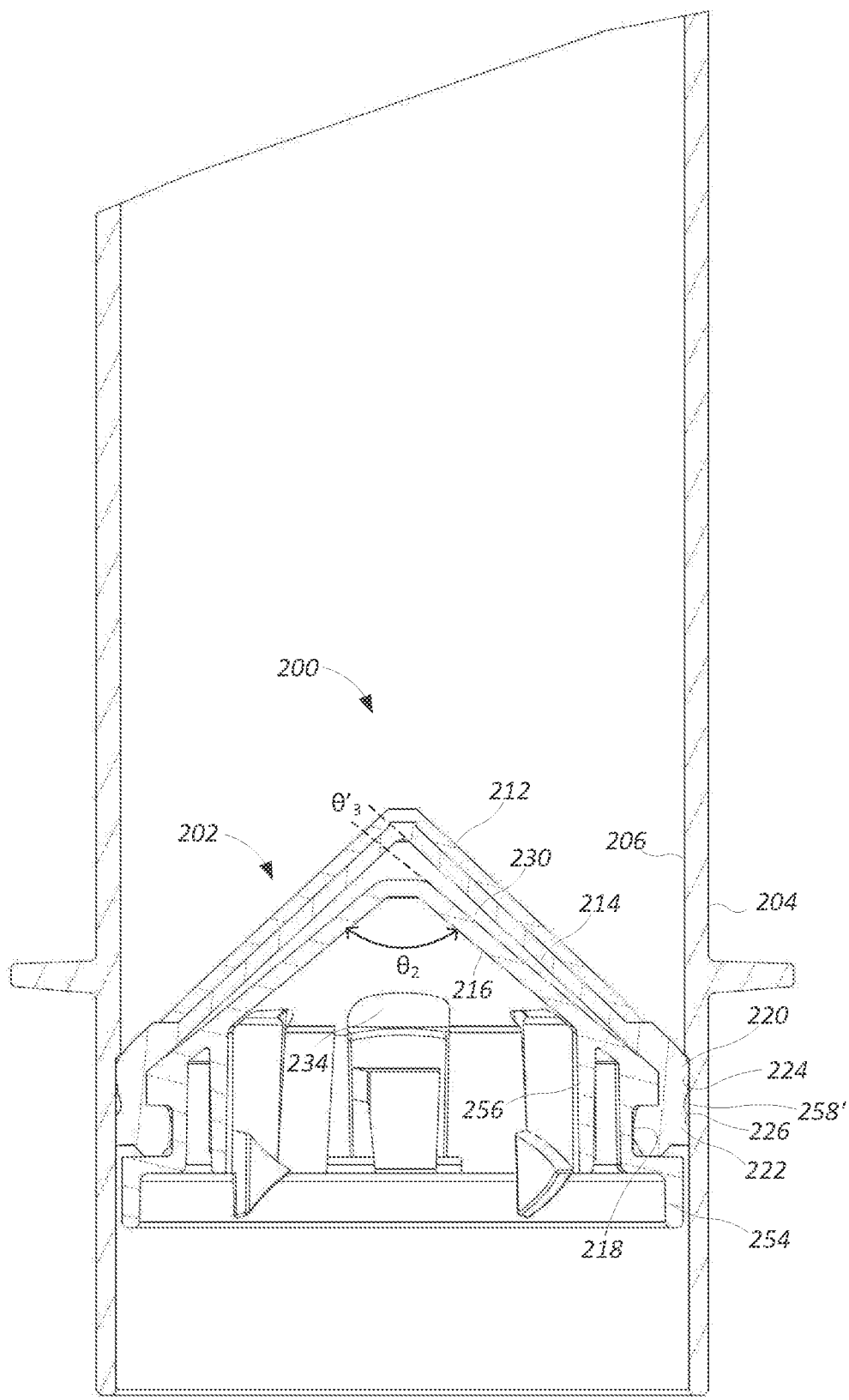
FIG. 13 is a sectional view of the syringe plunger system with dynamic seal shown in FIG. 12 under an initial state of compression, according to one aspect of the present disclosure.

FIG. 13 is a sectional view of the syringe plunger system 200 with a dynamic seal shown in FIG. 12 under an initial state of compression. A typical initial pressure range can vary from just above 0 to 100 PSI, for example. Under an initial state of compression, the angle $\theta'_3$ defined between the support ring 216 and the cover 214 is smaller than the angle $\theta_3$ shown in FIG. 12 due to the applied pressure of the fluid against the plunger cover 214. As shown in FIG. 13, the gap 258' defined between the support ring 216 and the inner wall 206 of the syringe barrel 204 is smaller than the gap 258 shown in FIG. 12 due to lateral forces exerted against the first and second annular slots 224, 226 by the first and second annular ribs 220, 222. The included angle $\theta_2$ remains substantially the same as the included angle $\theta_2$ shown in FIG. 12.

Figure 14:
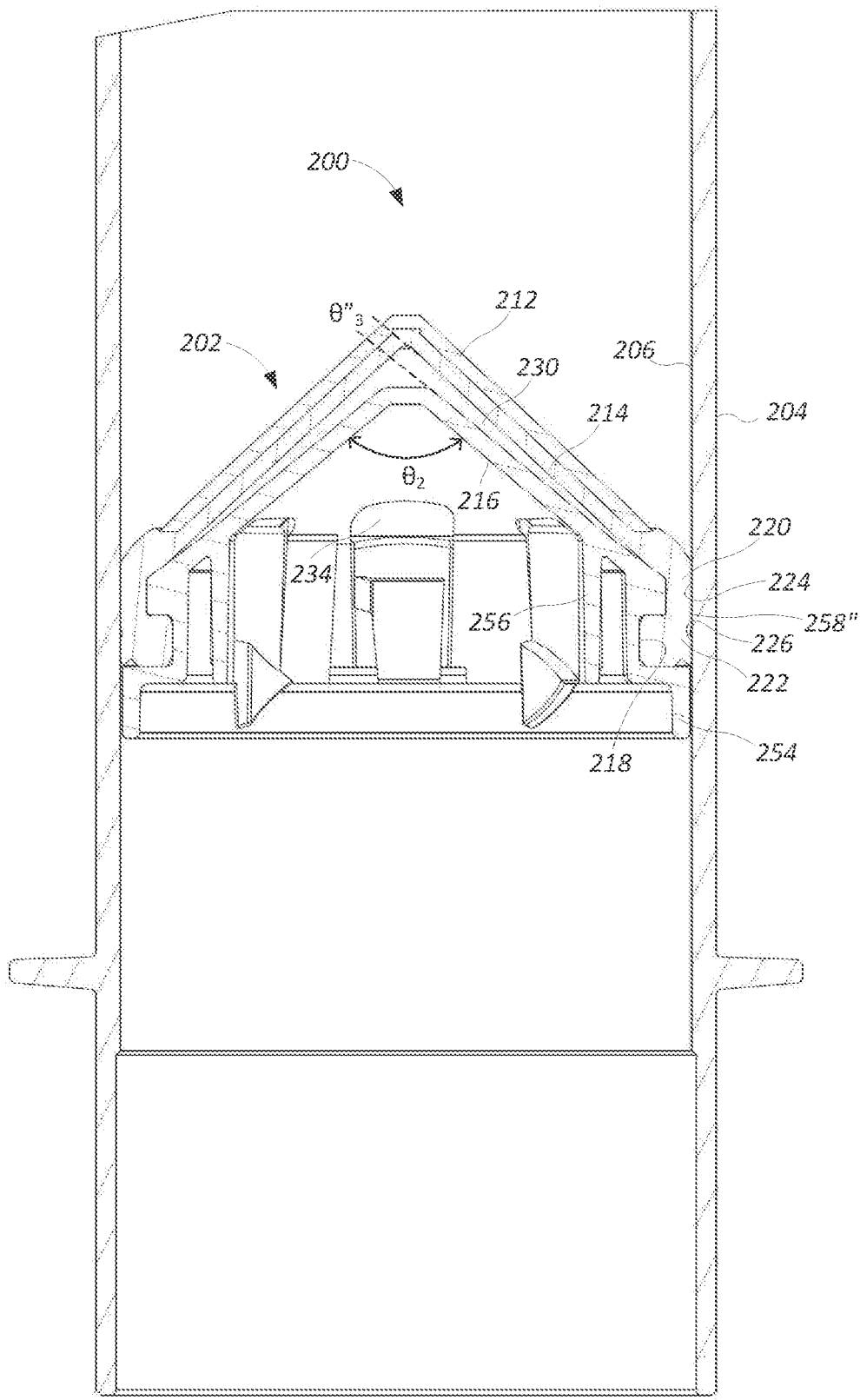
FIG. 14 is a sectional view of the syringe plunger system with a dynamic seal shown in FIG. 12 under operating injection pressure, according to one aspect of the present disclosure.

FIG. 14 is a partial sectional view of the syringe plunger system 200 with a dynamic seal shown in FIG. 12 under operating injection pressure. Operating injection pressures can vary from 150 to 800 PSI, depending on material and type of injection (e.g., CT or CV). Under operating pressure, the angle $\theta''_3$ defined between the support ring 216 and the cover 214 is smaller than the angle $\theta'_3$ defined between the support ring 216 and the cover 214 when the plunger 202 is in the initial state of compression. Accordingly, the gap 258" defined between the support ring 216 and the inner wall 206 of the syringe barrel 204 when the plunger 202 is under operating injection pressure is smaller than the gap 258' shown in FIG. 13 because of the additional radial forces exerted against the first and second annular slots 224, 226 by the first and second annular ribs 220, 222. Under operating injection pressures, the first and second annular ribs 220, 222 press against the side wall 206 to create a dynamic seal. As shown, the included angle $\theta_2$ remains substantially the same as the included angle $\theta_2$ shown in FIGS. 12 and 13.

Figure 15:
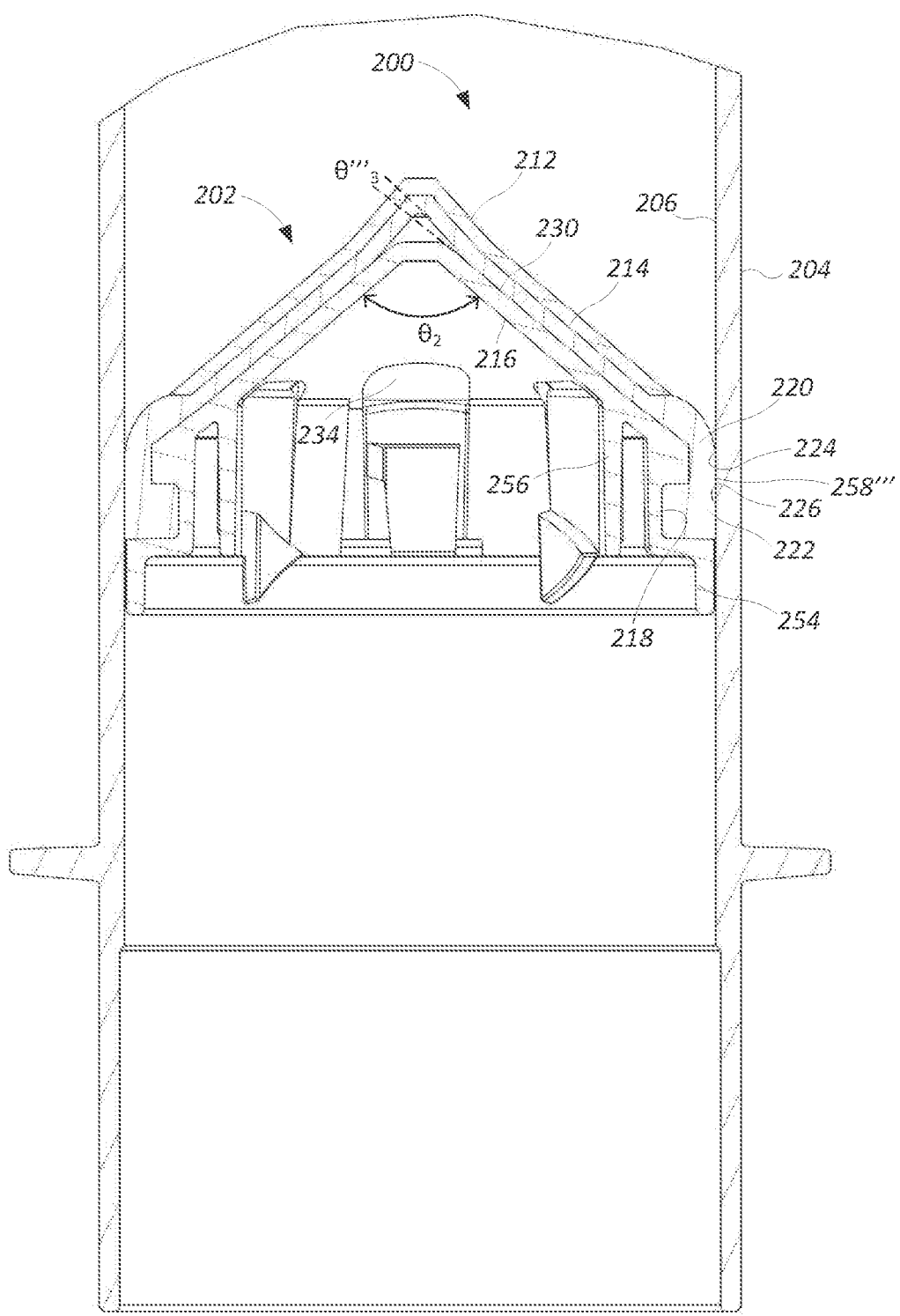
FIG. 15 is a sectional view of the syringe plunger system 200 with a dynamic seal shown in FIG. 12 under a state of compression near or beyond maximum injection pressure, according to one aspect of the present disclosure.

FIG. 15 is a partial sectional view of the syringe plunger system 200 with a dynamic seal shown in FIG. 12 under a state of compression near or beyond maximum injection pressure. Maximum injection pressure may vary from 500 to 1500 PSI, depending material and type of injection (e.g., CT or CV) and in some instances can be as high as 2000 PSI. Under high pressure conditions, the dynamic seal formed by the first and second annular ribs 220, 222 pressing against the side wall 206 may begin to leak. The threshold pressure at which this occurs is known as blow-by pressure. As shown in FIG. 15, under a maximum injection pressure conditions, the angle $\theta'''_3$ defined between the support ring 216 and the cover 214 is relatively small or near zero. As shown, the gap 258''' between the support ring 216 and the cover 214 has been reduced to near zero and substantially the entire air cavity 230 has been eliminated under the maximum injection pressure. As shown in FIG. 15, under maximum injection pressure conditions, the included angle $\theta_2$ remains substantially the same as the included angle $\theta_2$ shown in FIGS. 12-14.

FIG. 16 is a graphical representation 300 of the maximum pressure that the syringe plunger system 200 described in connection with FIGS. 4-15 can withstand after a sustained period of pressurization in accordance with one aspect. Pressure (PSI) is shown along the vertical axis and Time (mS) is shown along the horizontal axis. The tip 250 of the support ring 216 (FIGS. 6-11) was nominally about 0.005". The curve 302 represents the application of pressure to the syringe plunger system 200. During a first period T1, the pressure applied to the syringe plunger system 200 is ramped up (increased) from 0 PSI to about 355 PSI, which is approximately the operating pressure for one type of syringe plunger system 200. During a second period T2, the pressure of 355 PSI is held on the syringe plunger system 200. After a sustained period T2, during a third period T3, the pressure is ramped up (increased) until a failure, e.g., leaks, occurs. As shown by the curve 302, failure occurs at about 420 PSI during the third period T3.

Figure 17:
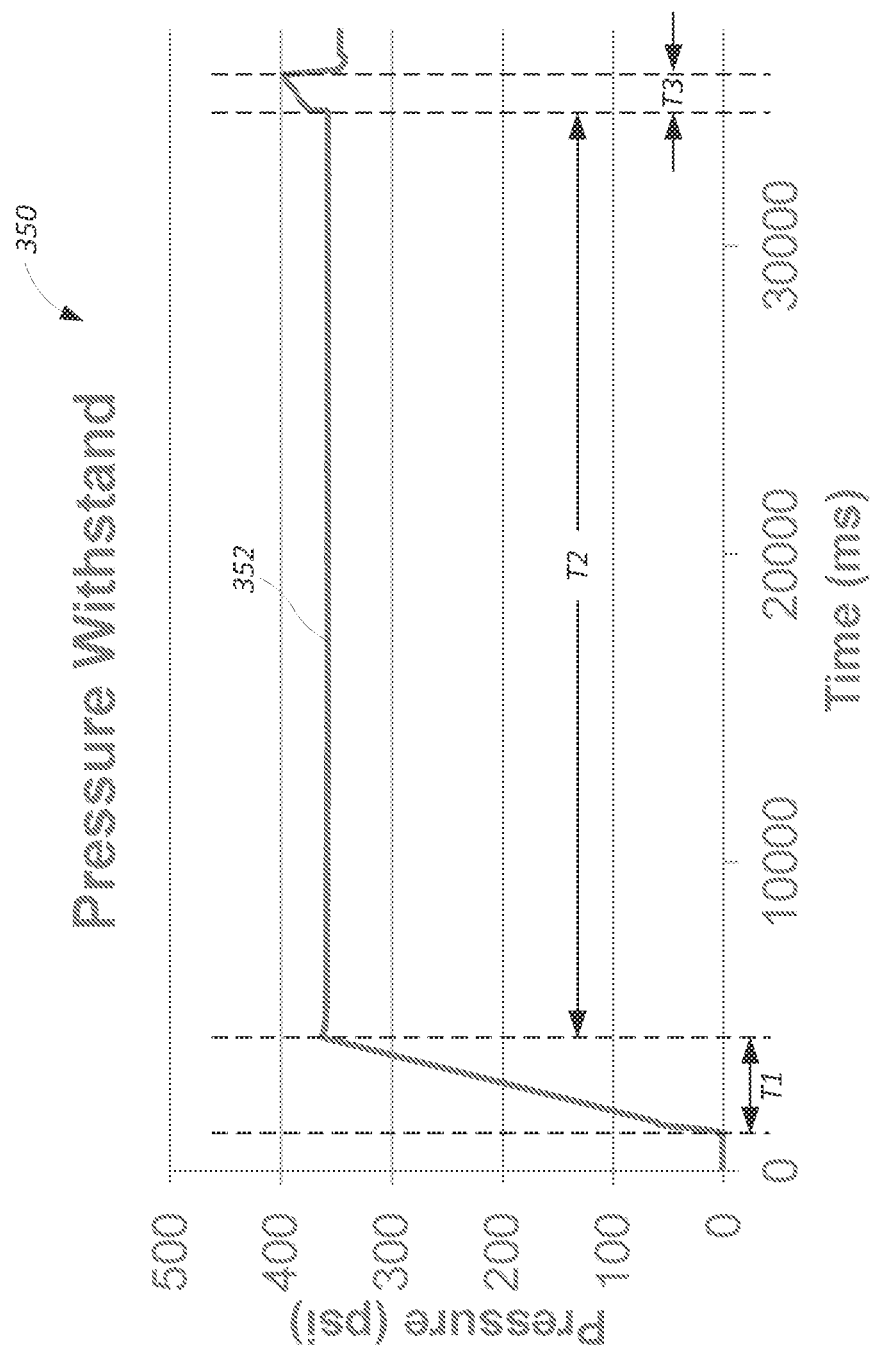
FIG. 17 is a graphical representation of how the maximum pressure that the syringe plunger system described in connection with FIGS. 4-15 withstands after a sustained period of pressurization, according to one aspect of the present disclosure.

FIG. 17 is a graphical representation 350 of the maximum pressure that the syringe plunger system 200 described in connection with FIGS. 4-15 can withstand after a sustained period of pressurization in accordance with another aspect. Pressure (PSI) is shown along the vertical axis and Time (mS) is shown along the horizontal axis. The tip 250 of the support ring 216 (FIGS. 6-11) was nominally about 0.005". The curve 352 represents the application of pressure to the syringe plunger system 200. During a first period T1, the pressure applied to the syringe plunger system 200 is ramped up (increased) from 0 PSI to a about 365 PSI, which is approximately the operating pressure for one type of syringe plunger system 200. During a second period T2, the pressure of 365 PSI is held on the syringe plunger system 200. After a sustained period T2, during a third period T3, the pressure is ramped up (increased) until a failure, e.g., leaks, occurs. As shown by the curve 352, failure occurs at about 400 PSI during the third period T3.

Figure 18:
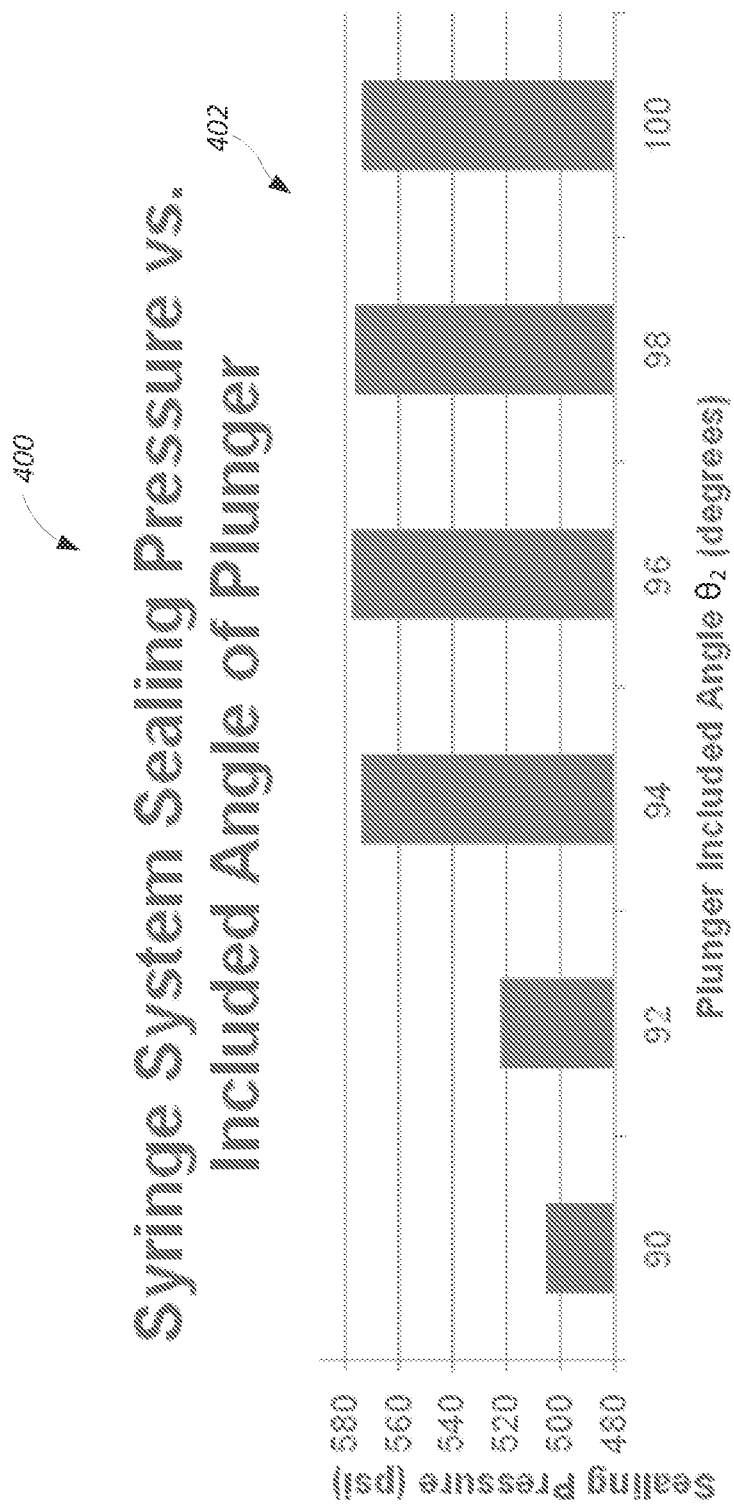
FIG. 18 is a graphical representation of the relationship of sealing pressure as a function of included angle of the plunger, according to one aspect of the present disclosure.

FIG. 18 is a graphical representation 400 of the relationship of sealing pressure as a function of included angle of the plunger system 200 described in connection with FIGS. 4-15 according to one aspect. Pressure (PSI) is shown along the vertical axis and Plunger Included Angle $\theta_2$ (Degrees) is shown along the horizontal axis. In this context, the plunger included angle is the included angle $\theta_2$ defined by the support ring 216 as described in connection with FIGS. 4-5B, 9, 11, and 12-15, for example. The bar graph 402 illustrates the maximum pressure that the syringe plunger system 200 can withstand as a function of the included angle $\theta_2$ of the support ring 216. As shown, at an included angle $\theta_2$ of 90° the maximum pressure is about 505 PSI. At an included angle $\theta_2$ of 92° the maximum pressure is about 520 PSI. At an included angle $\theta_2$ of 94° the maximum pressure is about 575 PSI. At an included angle $\theta_2$ of 96° the maximum pressure is about 590 PSI. At a n included angle $\theta_2$ of 98° the maximum pressure is about 580 PSI. And at an included angle $\theta_2$ of 100° the maximum pressure is about 575 PSI. Accordingly, for the example depicted in FIGS. 4-15, the data shows that an included angle $\theta_2$ in the range of 90°-100°, the optimal included angle $\theta_2$ is about 96° since this angle produces a dynamic seal that can withstand the maximum seal pressure required for certain applications. It will be appreciated, however, that the included angle $\theta_2$ can be optimized to provide dynamic seals that can withstand a variety of maximum injection pressures. Accordingly, the specific values of the included angle $\theta_2$ and corresponding maximum withstand pressure disclosed herein should not be considered as limiting the scope of the present disclosure.

Accordingly, the volume of the air cavity 230 (see FIGS. 4, 5A, and 12-15), which is defined by the included angle $\theta_2$ of the support ring 216 translates to sealing pressure of the dynamic seal. Another way to measure the effect of the dynamic seal is to increase the volume of air cavity 230 and measure the sealing pressure limit of the syringe plunger system 200. The graphical representation 400 shown in FIG. 18 shows how increasing the included angle $\theta_2$ of the support ring 216 increases (increasing the volume of the air cavity 230) the dynamic pressure seal limits of the syringe plunger system 200. The plunger 202 sealing capability eventually surpasses the material strength of the syringe barrel 204 at 96°, leading to a plateau in sealing pressure limit.

Figure 19:
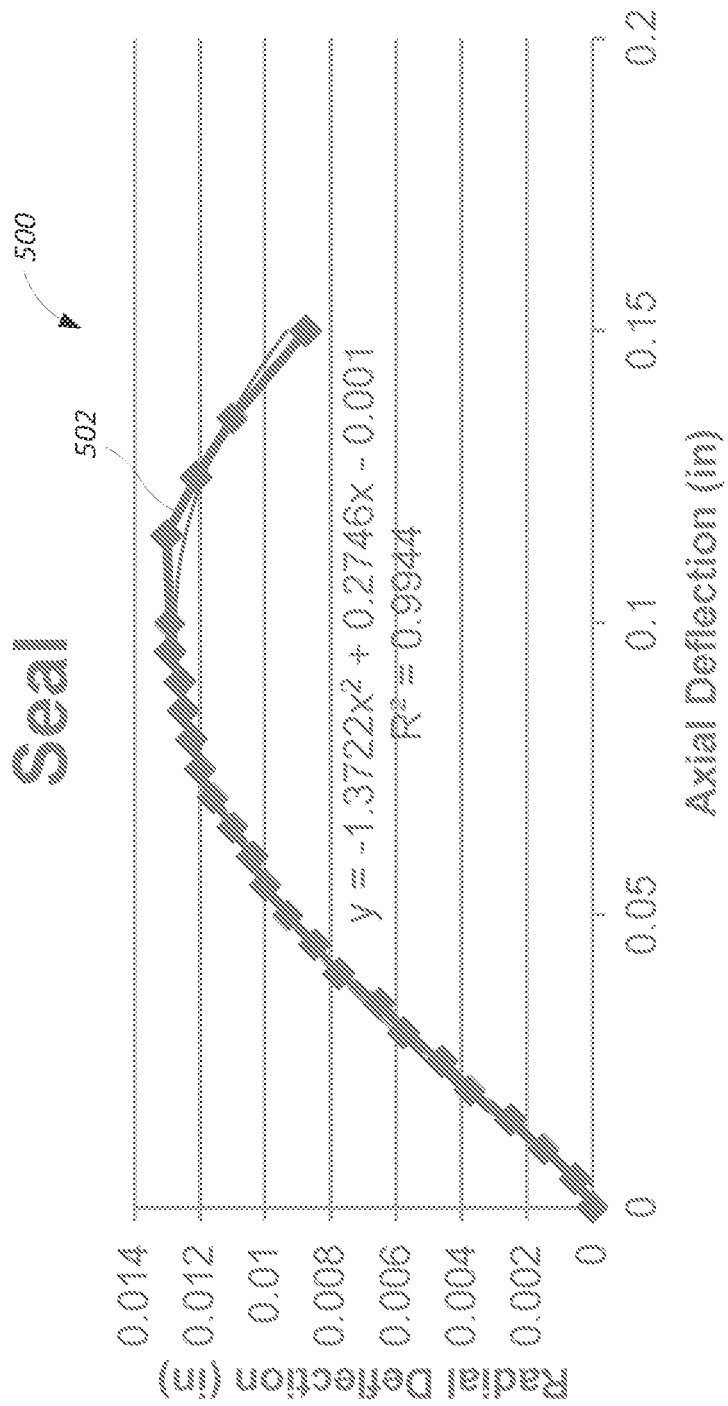
FIG. 19 is a graphical representation of an optimal gap size of an air cavity described for dynamic seal of a syringe plunger system, according to one aspect of the present disclosure.
Figure 8:
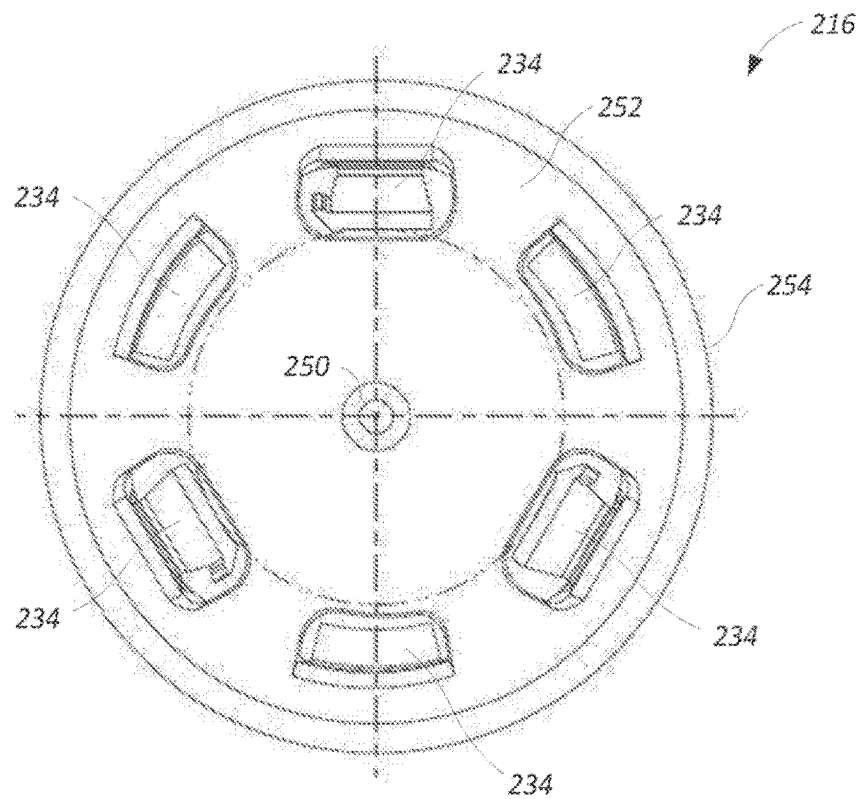
Figure 9:
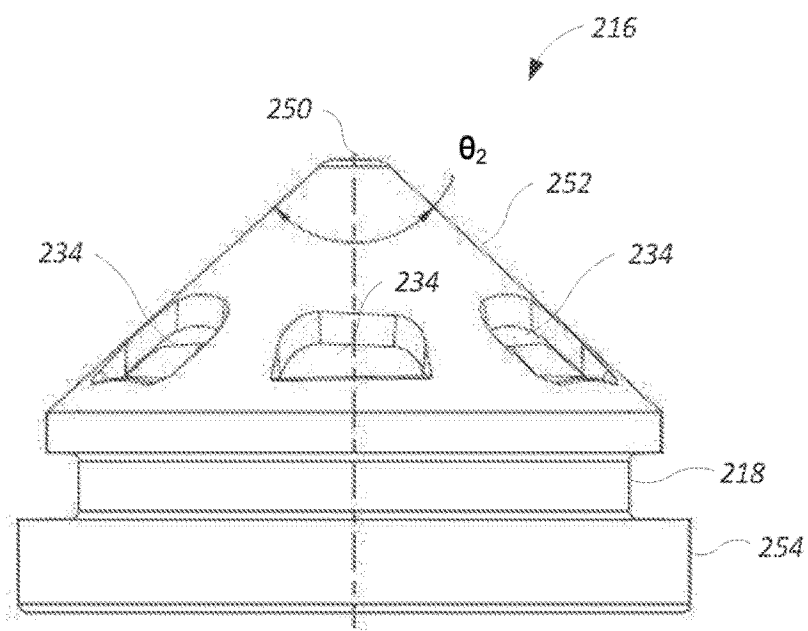
Figure 10:
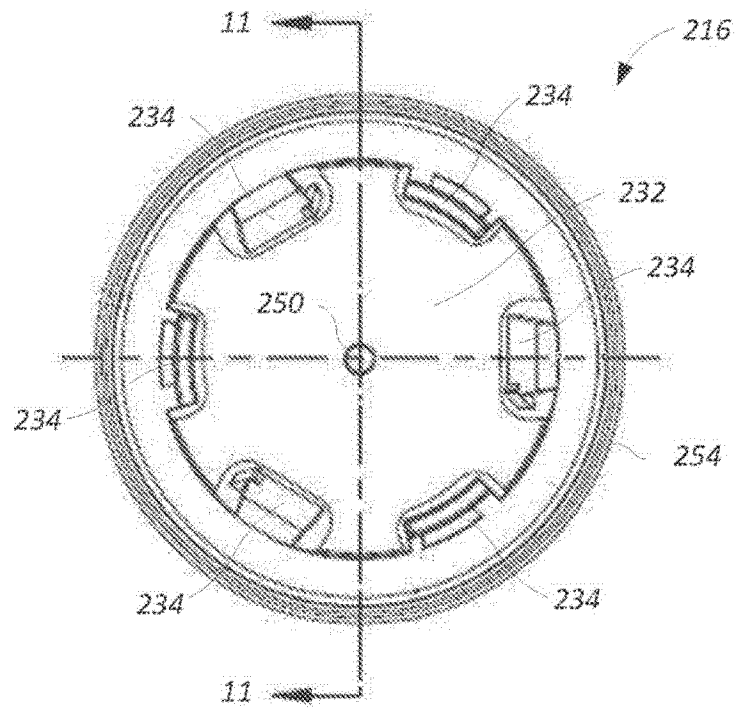
Figure 11:
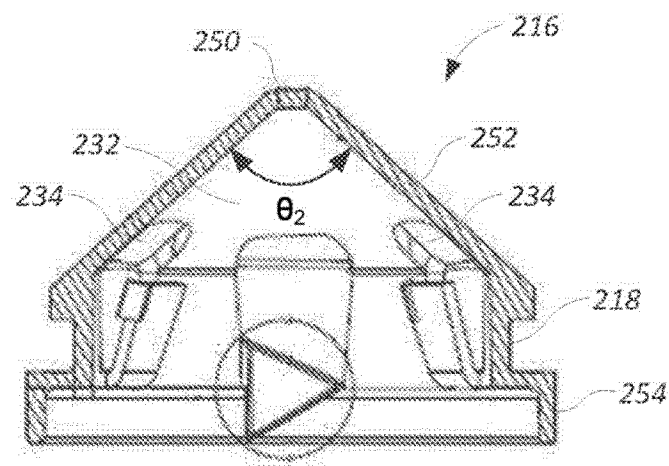

FIG. 19 is a graphical representation 500 of an optimal gap size of the air cavity 230 described in connection with FIGS. 4, 5A, and 12-15 for dynamic seal of the syringe plunger system 200 described in connection with FIGS. 4-15 according to one aspect of the present disclosure. Radial deflection (inches) is shown along the vertical axis and axial deflection (inches) is shown along the horizontal axis. The data points of the curve 502 can be used to develop an $n^{th}$ order polynomial equation that represents the conical dynamic seal for the syringe plunger system 200 according to one aspect of the present disclosure. The optimal gap size of the air cavity 230 can be calculated to produce the optimal effect of the dynamic seal. This optimal effect is equivalent to maximum added compression for sealing. One non-limiting example of this calculation is shown below. As the gap size of the air cavity 230 is increased, a peak compression is reached before the component collapses in on itself and the compression is actually reduced. Equation (1) below is one example of a $2^{nd}$ order equation derived from the data points of the curve 502 for a seal radius of 0.9944 inches.

$$y = 1.3722x^2 + 0.2746x - 0.001 \quad (1)$$

While various details have been set forth in the foregoing description, it will be appreciated that the various aspects of the syringe plunger with dynamic seal may be practiced without these specific details. For example, for conciseness and clarity selected aspects have been shown in schematic form rather than in detail.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in a form" in various places throughout the specification are not necessarily all referring to the same aspect. Furthermore, the particular features, structures or characteristics may be combined in any suitable manner in one or more aspects.

Although various forms have been described herein, many modifications, variations, substitutions, changes, and equivalents to those forms may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed forms. The following claims are intended to cover all such modification and variations.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Although various forms have been described herein, many modifications, variations, substitutions, changes, and equivalents to those forms may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed forms. The following claims are intended to cover all such modification and variations.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:
1. A plunger, comprising:
a support ring comprising a first conical cap;
a cover disposed over and coupled to the support ring, wherein the cover comprises a second conical cap and a a cylindrical side wall, wherein the cylindrical side wall comprises at least one annular rib; and
an air cavity defined between the first conical cap and the second conical cap, the air cavity defining a predetermined compliance volume such that when the plunger undergoes injection pressurization, the cover deforms and flexes into the compliance volume,
wherein a distal portion of the first conical cap forms an angle with a proximal portion of the second conical cap, and
wherein, due to the deforming and flexing of the cover, the angle between the distal portion of the first conical cap and the proximal portion of the second conical cap is smaller when the plunger is under pressure from an injection than when the plunger is not under pressure from the injection, and wherein the at least one annular rib is radially outwardly deflected against an inner wall of a syringe barrel when the angle is smaller.

2. The plunger of claim 1, further comprising a third conical cap disposed over a distal surface of the cover.

3. The plunger of claim 2, wherein the third conical cap comprises an overmold element.

4. The plunger of claim 1, wherein the at least one annular rib comprises first and second annular ribs on the cylindrical side wall.

5. The plunger of claim 1, wherein the cover further comprises:
an inner flange to engage an annular groove on the support ring between a shoulder and the first conical cap.

6. The plunger of claim 1, wherein the first conical cap of the support ring defines an included apex angle greater than about 90°.

7. The plunger of claim 6, wherein the first conical cap of the support ring defines an included apex angle greater than about 90° and less than about 120°.

8. The plunger of claim 1, wherein the angle defined between the first conical cap of the support ring and the second conical cap of the cover is greater than 0° and less than about 30°.

9. The plunger of claim 1, wherein a predetermined volume of the air cavity is selected in a range between 0.1 mL and 10 mL.

10. A syringe, comprising:
a barrel defining an inner wall; and
a plunger located within the inner wall of the barrel, the plunger comprising:
a support ring comprising a first conical cap;
a cover disposed over and coupled to the support ring, wherein the cover comprises a second conical cap and a cylindrical side wall, wherein the cylindrical side wall comprises at least one annular rib; and
an air cavity defined between the first conical cap and the second conical cap, the air cavity defining a predetermined compliance volume such that when the plunger undergoes injection pressurization, the cover deforms and flexes into the compliance volume,
wherein a distal portion of the first conical cap forms an angle with a proximal portion of the second conical cap, and
wherein, due to the deforming and flexing of the cover, the angle between the distal portion of the first conical cap and the proximal portion of the second conical cap is smaller when the plunger is under pressure from an injection than when the plunger is not under pressure from the injection, and wherein the at least one annular rib is radially outwardly deflected against the inner wall of the barrel when the angle is smaller.

11. The syringe of claim 10, wherein the plunger comprises a third conical cap disposed over the cover.

12. The syringe of claim 11, wherein the third conical cap comprises an overmold element.

13. The syringe of claim 10, wherein the at least one annular rib comprises first and second annular ribs on the cylindrical side wall that form a seal with the inner wall of the barrel.

14. The syringe of claim 10, wherein the cover further comprises:
an inner flange to engage an annular groove on the support ring between a shoulder and the first conical cap.

15. The syringe of claim 10, wherein the first conical cap of the support ring defines an included apex angle greater than about 90°.

16. The syringe of claim 15, wherein the first conical cap of the support ring defines an included apex angle greater than about 90° and less than about 120°.

17. The syringe of claim 10, wherein the angle defined between the first conical cap of the support ring and the second conical cap of the cover is greater than 0° and less than about 30°.

18. The syringe of claim 10, wherein a predetermined volume of the air cavity is selected in a range between 0.1 mL and 10 mL.

19. A method of making a plunger, the method comprising:
providing a support ring, the support ring comprising a first conical cap having a first apex angle, a shoulder, and an annular groove between the shoulder and the first conical cap;
attaching a cover to the support ring, the cover comprising a second conical cap having a second apex angle, a cylindrical side wall, and a flange to engage the annular groove of the support ring, wherein the cylindrical side wall comprises at least one annular rib; and
defining an air cavity between the first conical cap and the second conical cap based on a difference between the first apex angle and the second apex angle, the air cavity defining a predetermined compliance volume such that when the plunger undergoes injection pressurization, the cover deforms and flexes into the compliance volume,
wherein a distal portion of the first conical cap forms an angle with a proximal portion of the second conical cap, and
wherein, due to the deforming and flexing of the cover, the angle between the distal portion of the first conical cap and the proximal portion of the second conical cap is smaller when the plunger is under pressure from an injection than when the plunger is not under pressure from the injection, and wherein the at least one annular rib is radially outwardly deflected against an inner wall of a syringe barrel when the angle is smaller.

20. The method of claim 19, further comprising attaching a third conical cap to a distal portion of the second conical cap of the cover,
wherein the third conical cap comprises an overmolded element.

* * * * *

UNITED STATES PATENT AND TRADEMARK OFFICE
CERTIFICATE OF CORRECTION

| | | |
|---|---|---|
| PATENT NO. | : 11,351,306 B2 | |
| APPLICATION NO. | : 16/471300 | |
| DATED | : June 7, 2022 | |
| INVENTOR(S) | : Swantner et al. | |

It is certified that error appears in the above-identified patent and that said Letters Patent is hereby corrected as shown below:

In the Drawings
Replace Fig. 9 with Fig. 9 as shown on the attached page.
Replace Fig. 11 with Fig. 11 as shown on the attached page.

In the Specification
In Column 1, Line 60, delete "seal" and insert -- seal to --, therefor.
In Column 3, Line 40, delete "an d" and insert -- and --, therefor.
In Column 4, Line 27, delete "FIGURES" and insert -- BRIEF DESCRIPTION OF THE DRAWINGS --, therefor.
In Column 6, Line 42, delete "to" and insert -- into --, therefor.
In Column 8, Line 3, delete "no a" and insert -- no --, therefor.
In Column 8, Line 15, delete "of the of" and insert -- of the --, therefor.
In Column 9, Line 62, delete "easy of" and insert -- easy --, therefor.
In Column 9, Line 63, delete "injected molded." and insert -- injected and molded. --, therefor.
In Column 10, Line 8, delete "connect ion" and insert -- connection --, therefor.
In Column 11, Line 6, delete "include angle" and insert -- included angle --, therefor.
In Column 11, Line 22, delete "aperature 234." and insert -- aperture 234. --, therefor.
In Column 11, Line 56, delete "in" and insert -- is --, therefor.
In Column 12, Line 44, delete "depending" and insert -- depending on --, therefor.
In Column 13, Line 21, delete "to a" and insert -- to --, therefor.
In Column 13, Line 45, delete "a n" and insert -- an --, therefor.
In Column 14, Equation (1), Line 28, delete "$y=1.3722x^2+0.2746x-0.001$" and insert -- $y=-1.3722x^2+0.2746x-0.001$ --, therefor.
In Column 15, Line 14, delete "taken" and insert -- taken as --, therefor.

In the Claims
In Column 16, Line 46, in Claim 1, delete "a a" and insert -- a --, therefor.

Signed and Sealed this
Sixth Day of September, 2022

*Katherine Kelly Vidal*
Katherine Kelly Vidal
*Director of the United States Patent and Trademark Office*